United States Patent
Gangwar et al.

(10) Patent No.: US 7,968,586 B2
(45) Date of Patent: *Jun. 28, 2011

(54) CYTOTOXIC COMPOUNDS AND CONJUGATES

(75) Inventors: Sanjeev Gangwar, San Mateo, CA (US); Bilal Sufi, Santa Clara, CA (US)

(73) Assignee: Medarex, Inc., Princeton, NJ (US)

( * ) Notice: Subject to any disclaimer, the term of this patent is extended or adjusted under 35 U.S.C. 154(b) by 366 days.

This patent is subject to a terminal disclaimer.

(21) Appl. No.: 12/090,453

(22) PCT Filed: Nov. 9, 2006

(86) PCT No.: PCT/US2006/060711
§ 371 (c)(1),
(2), (4) Date: Apr. 16, 2008

(87) PCT Pub. No.: WO2007/059404
PCT Pub. Date: May 24, 2007

(65) Prior Publication Data
US 2008/0293800 A1  Nov. 27, 2008

Related U.S. Application Data

(60) Provisional application No. 60/735,657, filed on Nov. 10, 2005.

(51) Int. Cl.
*A61K 31/403* (2006.01)
*A61P 35/00* (2006.01)
*C07D 405/06* (2006.01)

(52) U.S. Cl. .................................... 514/411; 548/427

(58) Field of Classification Search ................... None
See application file for complete search history.

(56) References Cited

U.S. PATENT DOCUMENTS

| | | | |
|---|---|---|---|
| 4,169,888 A | 10/1979 | Hanka et al. |
| 4,391,904 A | 7/1983 | Litman et al. |
| 4,671,958 A | 6/1987 | Rodwell et al. |
| 4,816,567 A | 3/1989 | Cabilly et al. |
| 4,912,227 A | 3/1990 | Kelly et al. |
| 4,923,990 A | 5/1990 | Nakano et al. |
| 4,952,394 A | 8/1990 | Senter |
| 4,975,278 A | 12/1990 | Senter et al. |
| 4,978,757 A | 12/1990 | Kelly et al. |
| 4,994,578 A | 2/1991 | Ohba et al. |
| 5,037,993 A | 8/1991 | Ohba et al. |
| 5,070,092 A | 12/1991 | Kanda et al. |
| 5,084,468 A | 1/1992 | Saito et al. |
| 5,101,038 A | 3/1992 | Nakano et al. |
| 5,117,006 A | 5/1992 | Saito et al. |
| 5,137,877 A | 8/1992 | Kaneko et al. |
| 5,138,059 A | 8/1992 | Takahashi et al. |
| 5,147,786 A | 9/1992 | Feng et al. |
| 5,176,996 A | 1/1993 | Hogan et al. |
| 5,187,186 A | 2/1993 | Kanda et al. |
| 5,223,409 A | 6/1993 | Ladner et al. |
| 5,225,539 A | 7/1993 | Winter |
| 5,288,514 A | 2/1994 | Ellman |
| 5,324,483 A | 6/1994 | Cody et al. |
| 5,332,740 A | 7/1994 | Saito et al. |
| 5,332,837 A | 7/1994 | Kelly et al. |
| 5,334,528 A | 8/1994 | Stanker et al. |
| 5,403,484 A | 4/1995 | Ladner et al. |
| 5,427,908 A | 6/1995 | Dower et al. |
| 5,475,092 A | 12/1995 | Chari et al. |
| 5,495,009 A | 2/1996 | Matteucci et al. |
| 5,530,101 A | 6/1996 | Queen et al. |
| 5,545,806 A | 8/1996 | Lonberg et al. |
| 5,547,667 A | 8/1996 | Angelucci et al. |
| 5,569,825 A | 10/1996 | Lonberg et al. |
| 5,571,698 A | 11/1996 | Ladner et al. |
| 5,573,922 A | 11/1996 | Hoess et al. |
| 5,580,717 A | 12/1996 | Dower et al. |
| 5,585,089 A | 12/1996 | Queen et al. |
| 5,585,499 A | 12/1996 | Chari et al. |
| 5,587,161 A | 12/1996 | Burke et al. |
| 5,606,017 A | 2/1997 | Willner et al. |
| 5,622,929 A | 4/1997 | Willner et al. |
| 5,625,126 A | 4/1997 | Lonberg et al. |
| 5,629,430 A | 5/1997 | Terashima et al. |
| 5,633,425 A | 5/1997 | Lonberg et al. |
| 5,641,780 A | 6/1997 | Amishiro et al. |
| 5,660,829 A | 8/1997 | Burke et al. |
| 5,661,016 A | 8/1997 | Lonberg et al. |

(Continued)

FOREIGN PATENT DOCUMENTS

DE  10008089 A1  10/2001
(Continued)

OTHER PUBLICATIONS

Bae, M. et al., "Metalloprotease-specific poly(ethylene glycol) Methyl Ether-Peptide-Doxorubicin Conjugate for Targeting Anticancer Drug Delivery Based on Angiogenesis," Drugs Exptl. Clin. Res., vol. 29(1):15-23 (2003).
Baldwin, Thomas O. et al., "Cloning and Expression of the luxY Gene from Vibrio fischeri Strain Y-1 in *Escherichia coli* and Complete Amino Acid Sequence of the Yellow Fluorescent Protein," Biochemistry, vol. 29:5509-5515 (1990).
Batzer, Mark A. et al., "Enhanced evolutionary PCR using oligonucleotides with inosine at the 3'-terminus," Nucleic Acids Research, vol. 19(18):5081 (1991).
Berge, Stephen M. et al., "Pharmaceutical Salts," Journal of Pharmaceutical Sciences, vol. 66(1):1-19 (1977).
Bird, Robert E. et al., "Single-Chain Antigen-Binding Proteins," Science, vol. 242:423-426 (1988).
Bock, Louis C. et al., "Selection of single-stranded DNA molecules that bind and inhibit human thrombin," Nature, vol. 355:564-566 (1992).
Bouvier, Jacques et al., "Leishmanolysin: Surface Metalloproteinase of Leishmania," Methods in Enzymology, Academic Press, San Diego, Alan J. Baarrett (Ed.), vol. 248:614-633 (1995).

(Continued)

*Primary Examiner* — Kamal A Saeed
(74) *Attorney, Agent, or Firm* — Nelson Mullins Riley & Scarborough LLP; Jane E. Remillard, Esq.; Pankaj N. Desai

(57) ABSTRACT

The present disclosure provides cytoxic compounds useful as drugs or prodrugs and to drug-cleavable substrate conjugates where the drug and cleavable substrate are optionally linked through a self-immolative linker.

18 Claims, No Drawings

U.S. PATENT DOCUMENTS

| | | | |
|---|---|---|---|
| 5,686,237 A | 11/1997 | Al-Bayati | |
| 5,693,762 A | 12/1997 | Queen et al. | |
| 5,703,080 A | 12/1997 | Nakakura et al. | |
| 5,712,374 A | 1/1998 | Kuntsmann et al. | |
| 5,714,586 A | 2/1998 | Kunstmann et al. | |
| 5,739,116 A | 4/1998 | Hamann et al. | |
| 5,739,350 A | 4/1998 | Kelly et al. | |
| 5,770,429 A | 6/1998 | Lonberg et al. | |
| 5,773,001 A | 6/1998 | Hamann et al. | |
| 5,773,435 A | 6/1998 | Kadow et al. | |
| 5,786,377 A | 7/1998 | Garcia et al. | |
| 5,786,486 A | 7/1998 | Fukuda et al. | |
| 5,789,650 A | 8/1998 | Lonberg et al. | |
| 5,814,318 A | 9/1998 | Lonberg et al. | |
| 5,846,545 A | 12/1998 | Chari et al. | |
| 5,874,299 A | 2/1999 | Lonberg et al. | |
| 5,877,296 A | 3/1999 | Hamann et al. | |
| 5,877,397 A | 3/1999 | Lonberg et al. | |
| 5,885,793 A | 3/1999 | Griffiths et al. | |
| 5,939,598 A | 8/1999 | Kucherlapati et al. | |
| 5,962,216 A | 10/1999 | Trouet et al. | |
| 5,969,108 A | 10/1999 | McCafferty et al. | |
| 5,985,908 A | 11/1999 | Boger | |
| 6,060,608 A | 5/2000 | Boger | |
| 6,066,742 A | 5/2000 | Fukuda et al. | |
| 6,075,181 A | 6/2000 | Kucherlapati et al. | |
| 6,103,236 A | 8/2000 | Suzawa et al. | |
| 6,114,598 A | 9/2000 | Kucherlapati et al. | |
| 6,130,237 A | 10/2000 | Denny et al. | |
| 6,132,722 A | 10/2000 | Siemers et al. | |
| 6,143,901 A | 11/2000 | Dervan | |
| 6,150,584 A | 11/2000 | Kucherlapati et al. | |
| 6,162,963 A | 12/2000 | Kucherlapati et al. | |
| 6,172,197 B1 | 1/2001 | McCafferty et al. | |
| 6,180,370 B1 | 1/2001 | Queen et al. | |
| 6,194,612 B1 | 2/2001 | Boger et al. | |
| 6,214,345 B1 | 4/2001 | Firestone et al. | |
| 6,262,271 B1 | 7/2001 | Boger | |
| 6,281,354 B1 | 8/2001 | Boger | |
| 6,310,209 B1 | 10/2001 | Boger | |
| 6,329,497 B1 | 12/2001 | Boger | |
| 6,342,480 B1 | 1/2002 | Trouet et al. | |
| 6,486,326 B2 | 11/2002 | Boger | |
| 6,512,101 B1 | 1/2003 | King et al. | |
| 6,521,404 B1 | 2/2003 | Griffiths et al. | |
| 6,534,660 B1 | 3/2003 | Yongxin et al. | |
| 6,544,731 B1 | 4/2003 | Griffiths et al. | |
| 6,548,530 B1 | 4/2003 | Boger | |
| 6,555,313 B1 | 4/2003 | Griffiths et al. | |
| 6,555,693 B2 | 4/2003 | Ge et al. | |
| 6,566,336 B1 | 5/2003 | Sugiyama et al. | |
| 6,593,081 B1 | 7/2003 | Griffiths et al. | |
| 6,630,579 B2 | 10/2003 | Chari et al. | |
| 6,759,509 B1 | 7/2004 | King et al. | |
| 6,762,179 B2 | 7/2004 | Cochran et al. | |
| 6,884,869 B2 | 4/2005 | Senter et al. | |
| 6,897,034 B2 | 5/2005 | Bebbington et al. | |
| 6,946,455 B2 | 9/2005 | Sugiyama et al. | |
| 7,087,600 B2 | 8/2006 | Ng et al. | |
| 7,091,186 B2 | 8/2006 | Senter et al. | |
| 7,115,573 B2 | 10/2006 | Pickford et al. | |
| 7,129,261 B2 | 10/2006 | Ng et al. | |
| 7,214,663 B2 | 5/2007 | Bebbington et al. | |
| 7,223,837 B2 | 5/2007 | De Groot et al. | |
| 7,304,032 B2 | 12/2007 | Bebbington et al. | |
| 7,329,507 B2 | 2/2008 | Pickford et al. | |
| 7,517,903 B2 * | 4/2009 | Chen et al. | 514/411 |
| 2002/0082424 A1 | 6/2002 | Boger | |
| 2002/0142955 A1 | 10/2002 | Dubois et al. | |
| 2003/0050331 A1 | 3/2003 | Ng et al. | |
| 2003/0064984 A1 | 4/2003 | Ng et al. | |
| 2003/0073852 A1 | 4/2003 | Ng et al. | |
| 2003/0083263 A1 | 5/2003 | Doronina et al. | |
| 2003/0096743 A1 | 5/2003 | Senter et al. | |
| 2003/0130189 A1 | 7/2003 | Senter et al. | |
| 2004/0121940 A1 | 6/2004 | De Groot et al. | |
| 2005/0014700 A1 | 1/2005 | Boger | |
| 2005/0026987 A1 | 2/2005 | Boger | |
| 2005/0239713 A1 | 10/2005 | Domling et al. | |
| 2005/0249740 A1 | 11/2005 | Domling et al. | |
| 2005/0272798 A1 | 12/2005 | Ng et al. | |
| 2006/0229253 A1 | 10/2006 | Doronina et al. | |

FOREIGN PATENT DOCUMENTS

| | | |
|---|---|---|
| EP | 0154445 A1 | 9/1985 |
| EP | 0360609 A2 | 3/1990 |
| EP | 0386563 A1 | 9/1990 |
| EP | 0537575 A1 | 4/1993 |
| EP | 0689845 B1 | 1/1996 |
| EP | 1243276 A1 | 9/2002 |
| WO | WO-88/04659 A2 | 6/1988 |
| WO | WO-90/13641 A1 | 11/1990 |
| WO | WO-90/15065 A1 | 12/1990 |
| WO | WO-91/04753 | 4/1991 |
| WO | WO-91/06556 A1 | 5/1991 |
| WO | WO-91/06626 A2 | 5/1991 |
| WO | WO-91/06629 A1 | 5/1991 |
| WO | WO-91/09865 A1 | 7/1991 |
| WO | WO-91/11535 A1 | 8/1991 |
| WO | WO-91/13080 A1 | 9/1991 |
| WO | WO-91/19813 A1 | 12/1991 |
| WO | WO-92/09705 A1 | 6/1992 |
| WO | WO-92/10590 A1 | 6/1992 |
| WO | WO-92/14843 A1 | 9/1992 |
| WO | WO-96/10405 | 4/1996 |
| WO | WO-97/12862 | 4/1997 |
| WO | WO-97/32850 A1 | 9/1997 |
| WO | WO-97/45411 | 12/1997 |
| WO | WO-9811101 | 3/1998 |
| WO | WO-98/25900 | 6/1998 |
| WO | WO-98/52925 A1 | 11/1998 |
| WO | WO-99/19298 A1 | 4/1999 |
| WO | WO-99/29642 A1 | 6/1999 |
| WO | WO-00/33888 | 6/2000 |
| WO | WO-01/16104 | 3/2001 |
| WO | WO-01/16324 A2 | 3/2001 |
| WO | WO-01/49698 A1 | 7/2001 |
| WO | WO-01/74898 A2 | 10/2001 |
| WO | WO-01/83482 | 11/2001 |
| WO | WO-01/85733 A1 | 11/2001 |
| WO | WO-01/95943 A2 | 12/2001 |
| WO | WO-01/95945 A2 | 12/2001 |
| WO | WO-02/00263 A2 | 1/2002 |
| WO | WO-02/15700 | 2/2002 |
| WO | WO-02/43478 A2 | 6/2002 |
| WO | WO-02/083180 A1 | 10/2002 |
| WO | WO-02/088172 A2 | 11/2002 |
| WO | WO-02/100353 A2 | 12/2002 |
| WO | WO-02096910 | 12/2002 |
| WO | WO-03/022806 A2 | 3/2003 |
| WO | WO-03/026577 A2 | 4/2003 |
| WO | WO-03/086318 | 10/2003 |
| WO | WO-03/087055 | 10/2003 |
| WO | WO-2004/005326 A2 | 1/2004 |
| WO | WO-2004/005327 A1 | 1/2004 |
| WO | WO-2004/032828 | 4/2004 |
| WO | WO-2004/043493 A1 | 5/2004 |
| WO | WO-2004/101767 A2 | 11/2004 |
| WO | WO-2005/112919 | 12/2005 |
| WO | WO-2006/110476 | 10/2006 |
| WO | WO-2007/089149 | 8/2007 |

OTHER PUBLICATIONS

Broder, Samuel et al., "Antiretroviral Therapy in AIDS," Annals of Internal Medicine, vol. 113(8):604-618 (1990).

Bundgaard, Hans et al., "N-Sulfonyl Imidates as a Novel Prodrug Form for an Ester Function or a Sulfonamide Group," J. Med. Chem., vol. 31:2066-2069 (1988).

Campbell, Jeannette M. et al., "Oligodeoxynucleoside phosphorothioate stability in subcellular extracts, culture media, sera and cerebrospinal fluid," Journal of Biochemical and Biophysical Methods, vol. 20:259-267 (1990).

Chau, Ying et al., "Synthesis and Characterization of Dextran-Peptide-Methotrexate Conjugates for Tumor Targeting via Mediation by Matrix Metalloproteinase II and Matrix Metalloproteinase IX," Bioconjugate Chem., vol. 15:931-941 (2004).

Chen, Chixu et al., "'Analogous' Organic Synthesis of Small Compound Libraries: Validation of Combinatorial Chemistry in Small-Molecule Synthesis," J. Am. Chem., vol. 116:2661-2662 (1994).

Ch'ng, J. Lai C. et al., "Antisense RNA complementary to 3' coding and noncoding sequences of creatine kinase is a potent inhibitor of translation in vivo," Proc. Natl. Acad. Sci. USA, vol. 86:10006-10010 (1989).

Chrisey, Linda A. et al., "Covalent attachment of synthetic DNA to self-assembled monolayer films," Nucleic Acids Research, vol. 24(15):3031-3039 (1996).

Cole, S.P.C. et al., "The EBV-Hybridoma Technique and its Application to Human Lung Cancer," Monoclonal Antibodies and Cancer Therapy, Alan R. Liss, Inc., New York, Ralph A. Reisfeld (ed.), pp. 77-96 (1985).

Coussens, Lisa M. et al., "Inflammatory mast cells up-regulate angiogenesis during squamous epithelial carcinogenesis," Genes & Development, vol. 13:1382-1397 (1999).

Dagle, John M. et al., "Targeted degradation of mRNA in Xenopus oocytes and embryos directed by modified oligonucleotides: studies of An2 and cyclin in embryogenesis," Nucleic Acids Research, vol. 18(16):4751-4757 (1990).

Dano, K. et al., "Plasminogen Activators, Tissue Degradation, and Cancer," Advances in Cancer Research, Academic Press, Inc., Orlando, George Klein (Ed.), vol. 44:139-266 (1985).

Dean, Peter D. G. et al., "Affinity Chromatography of Enzymes," Affinity Chromatogr. Proc. Int. Symp., pp. 25-38 (1978).

Dunn, Richard L., "Polymeric Matrices," Polymeric Drugs and Drug Delivery Systems, American Chemical Society, Richard L. Dunn (Ed.), Chpt. 2, pp. 11-23 (1991).

Dunn, Ben M. et al., "Subsite Preferences of Retroviral Proteinases," Methods in Enzymology, Retroviral Proteases, Academic Press, San Diego, Lawrence C. Kuo (Ed.), vol. 241:254-278 (1994).

Ellington, Andrew D. et al., "In vitro selection of RNA molecules that bind specific ligands," Nature, vol. 346:818-822 (1990).

Farooqui, Akhlaq A., "Purification of Enzymes by Heparin-Sepharose Affinity Chromatography," Journal of Chromatography, vol. 184:335-345 (1980).

Froehler, B. et al., "Phosphoramidate analogues of DNA: synthesis and thermal stability of heteroduplexes," Nucleic Acids Research, vol. 16(11):4831-4839 (1988).

Guilford, H., "Bioaffinity Chromatography," High Perform. Liq. Chromatogr., Simpson (Ed.), pp. 193-206 (1976).

Hardy, J. et al., "Genetic Variability and Alzheimer's Disease," AMyloid Protein Precursor in Development, Aging and Alzheimer's Disease, C.L. Masters et al. (Eds.), Springer-Verlag, Berlin, pp. 190-198 (1994).

Heller, Adam, "Electrical Wiring of Redox Enzymes," Acc. Chem. Res., vol. 23:128-134 (1990).

Huang, Jun-Xiong et al., "Applications of Preparative High-performance Liquid Chromatography to the Separation and Purification of Peptides and Proteins," Journal of Chromatography, vol. 492:431-469 (1989).

Huston, James S. et al., "Protein engineering of antibody binding sites: Recovery of specific activity in an anti-digoxin single-chain Fv analogue produced in Escherichia coli," Proc. Natl. Acad. Sci. USA, vol. 85:5879-5883 (1988).

Kohler, G. et al., "Continuous cultures of fused cells secreting antibody of predefined specificity," Nature, vol. 256:495-497 (1975).

Kohler, G. et al., "Derivation of specific antibody-producing tissue culture and tumor lines by cell fusion," Eur. J. Immunol., vol. 6:511-519 (1976).

Kozbor, Danuta et al., "The production of monoclonal antibodies from human lymphocytes," Immunology Today, vol. 4(3):72-79 (1983).

Lee, Dennis et al., "A Substrate Combinatorial Array for Caspases," Bioorganic & Medicinal Chemistry Letters, vol. 9:1667-1672 (1999).

Lee, Sheau-Ling et al., "Activation of Hepatocyte Growth Factor and Urokinase/Plasminogen Activator by Matriptase, an Epithelial Membrane Serine Protease," The Journal of Biological Chemistry, vol. 275(47):36720-36725 (2000).

Lee, C-Y. et al., "Principles of Multi-Enzyme Purification by Affinity Chromatography," Enzyme Engineering, Plenum Press, New York, Georges B. Broun et al., (eds.), vol. 4:441-442 (1978).

Letsinger, Robert L. et al., "Cationic Oligonucleotides," J. Am. Chem., vol. 110:4471-4471 (1988).

Levine, Leonard D. et al., "Isolation and Characterization of a Photoprotein, 'Phialidin,' and a Spectrally Unique Green-fluorescent Protein from the Bioluminescent Jellyfish Phialidium Gregarium," Comp. Biochem. Physiol., vol. 72B:77-85 (1982).

Liu, Shihui et al., "Tumor Cell-selective Cytotoxicity of Matrix Metalloproteinase-activated Anthrax Toxin," Cancer Research, vol. 60:6061-6067 (2000).

Loreau, Nadine et al., "Blockage of AMV reverse transcriptase by antisense oligodeoxynucleotides," FEBS, vol. 274:1,2:53-56 (1990).

Macaya, Roman F. et al., "Thrombin-binding DNA aptamer forms a unimolecular quadruplex structure in solution," Proc. Natl. Acad. Sci. USA, vol. 90:3745-3749 (1993).

Matayoshi, Edmund D. et al., "Novel Fluorogenic Substrates for Assaying Retroviral Proteases by Resonance Energy Transfer," Science, vol. 247:954-958 (1990).

Matteucci, Mark et al., "Deoxyoligonucleotides Bearing Neutral Analogues of Phosphodiester Linkages Recognize Duplex DNA via Triple-Helix Formation," J. Am. Chem., vol. 113:7767-7768 (1991).

Molino, Marina et al., "Interactions of Mast Cell Tryptase with Thrombin Receptors and PAR-2," The Journal of Biological Chemistry, vol. 272(7):4043-4049 (1997).

Nielsen, Peter E. et al., "Sequence-Selective Recognition of DNA by Strand Displacement with a Thymine-Substituted Polyamide," Science, vol. 254:1497-1500 (1991).

Nishikawa, A.H. et al., "Affinity Chromatography of Plamsa Proteins, An Overview," Proc. Int. Workshop Technol. Protein Sep. Improv. Blood Plasma Franctionation, Sandberg (ed.), pp. 422-435 (1977).

Nishikawa, A. Hirotoshi et al., "Affinity purification of enzymes," Chemtech, vol. 5(9):564-571 (1975).

Norris, Belinda J. et al., "Nucleotide sequence of a cDNA clone encoding the precursor of the peridinin-chlorophyll α-binding protein from the dinoflagellate Symbiodinium sp.," Plant Molecular Biology, vol. 24:673-677 (1994).

Ohtsuka, Eiko et al., "An Alternative Approach to Deoxyoligonucleotides as Hybridization Probes by Insertion of Deoxyinosine at Ambiguous Codon Positions," The Journal of Biological Chemistry, vol. 260(5):2605-2608 (1985).

Ostrove, Steven, "Affinity Chromatography: General Methods," Methods in Enzymology, vol. 182:357-370 (1990).

Rano, Thomas A. et al., "A combinatorial approach for determining protease specificities: application to interleukin-1β converting enzyme (ICE)," Chemistry & Biology, vol. 4:149-155 (1997).

Ribatti, Domenico et al., "Angiogenesis and Mast Cell Density with Tryptase Activity Increase Simultaneously with Pathological Progression in B-Cell Non-Hodgkin's Lymphomas," Int. J. Cancer, vol. 85:171-175 (2000).

Rossolini, Gian Maria et al., "Use of deoxyinosine-containing primers vs degenerate primers for polymerase chain reaction based on ambiguous sequence information," Molecular and Cellular Probes, vol. 8:91-98 (1994).

Seidah, Nabil G. et al., "Pro-Protein Convertases of Subtilisin/Kexin Family," Methods in Enzymology, vol. 244:175-189 (1994).

Smith, Michelle C. et al., "Purification and Kinetic Characterization of Human Cytomegalovirus Assemblin," Methods in Enzymology, vol. 244:412-423 (1994).

Stack, M. Sharon et al., "Human Mast Cell Tryptase Activates Single-chain Urinary-type Plasminogen Activator (Pro-urokinase)," The Journal of Biological Chemistry, vol. 259(13):9416-9419 (1994).

Stein, C.A. et al., "Oligodeoxynucleotides as Inhibitors of Gene Expression: A Review," Cancer Research, vol. 48:2659-2668 (1988).

Takanami, Iwao et al., "Mast Cell Density Is Associated with Angiogenesis and Poor Prognosis in Pulmonary Adenocarcinoma," Cancer, vol. 88(12):2686-2692 (2000).

Tam, Elizabeth K. et al., "Degradation of Airway Neuropeptides by Human Lung Tryptase," Am. J. Respir. Cell Mol. Biol., vol. 3:27-32 (1990).

Thornberry, Nancy A., "Interleukin-1β Converting Enzyme," Methods in Enzymology, vol. 244:615-631 (1994).

Toth, Tibor et al., "Cutaneous Malignant Melanoma: Correlation Between Neovascularization and Peritumor Accumulation of Mast Cells Overexpressing Vascular Endothelial Growth Factor," Human Pathology, vol. 31(8):955-960 (2000).

van der Krol, Alexander R. et al., "Modulation of Eukaryotic Gene Expression by Complementary RNA or DNA Sequences," BioTechniques, vol. 6(10):958-976 (1988).

Wang, Ke Yu et al., "A DNA Aptamer Which Binds to and Inhibits Thrombin Exhibits a New Structural Motif for DNA," Biochemistry, vol. 32:1899-1904 (1993).

Ward, E. Sally et al., "Binding activities of a repertoire of single immunoglobulin variable domains secreted from *Escherichia coli*," Nature, vol. 341:544-546 (1989).

Ward, William W. et al., "Spectral Perturbations of the Aequorea Green-fluorescent Protein," Photochem. Photobiol., vol. 35:803-808 (1982).

Warpehoski, Martha A., "Dissecting the complex structure of CC-1065," Drugs of the Future, vol. 16(2):131-141 (1991).

Weber, Joseph M. et al., "Adenovirus Endopeptidases," Methods in Enzymology, vol. 244:595-604 (1994).

Wilbans, Sigurd M. et al., "Rod Structure of a Phycoerythrin II-containing Phycobilisome. I. Organization and Sequence of the Gene Cluster Encoding the Major Phycobiliprotein and Components in the Genome of Marine Synechococcus SP.," The Journal of Biological Chemistry, vol. 268(2):1226-1235 (1993).

Zimmerman, M. et al., "Sensitive Assays for Trypsin, Elastase, and Chymotrypsin Using New Fluorogenic Substrates," Analytical Biochemistry, vol. 78:47-51 (1977).

Aristoff, Paul A. et al., "Synthesis and Biochemical Evaluation of the CBI-PDE-I-dimer, a Benzannelated Analog of (+)-CC-1065 That Also Produces Delayed Toxicity in Mice," J. Med. Chem., 1993, 36:1956-1963.

Boger, Dale L. et al., "1,2,9,9a-Tetrahydrocyclopropa[c]benz[e]indol-4-one (CBI) Analogs of CC-1065 and the Duocarmycins: Synthesis and Evaluation," 1995, 3(11): 1429-1453.

Boger, Dale L. et al., "CC-1065 and the Duocarmycins: Synthetic Studies," Chemical Reviews, 1997, 97(3):title page, 787-828.

Boger, Dale L. et al., "CC-1065 and the Duocarmycins: Understanding Their Biological Function Through Mechanistic Studies," Angew. Chem. Int. Ed. Engl. 1996, 35:title page, 1438-1474.

Boger, Dale L. et al., "DNA Alkylation Properties of the Duocarmycisn: (+)-Duocarmycin A, Epi-(−)-Duocarmycin A, Ent-(−)-Duocarmycin A and Epi,Ent-(−)-Duocarmycin A," Bioogranic & Medicinal Chemistry Letters, 1992, 2(7):759-765.

Boger, Dale L. et al., "Duocarmycin SA Shortened, Simplified, and Extended Agents: A Systematic Examination of the Role of the DNA Binding Subunit," J. Am. Chem. Soc., 1997, 119(21):4977-4986.

Boger, Dale L. et al., "Duocarmycin-Pyrindamycin DNA Alkylation Properties and Identification, Synthesis, and Evaluation of Agents Incorporating the Pharmacophore of the Duocarmycin-Pyrindamycin Alkylation Subunit. Identification of the CC-1065-Duocarmycin Common Pharmacophore," J. Am. Chem. Soc., 1990, 112:8961-8971.

Boger, Dale L. et al., "Isolation and Characterization of the Duocarmycin-Adenine DNA Adduct," J. Am. Chem. Soc., 1991, 113:6645-6649.

Boger, Dale L. et al., "Reversibility of the Duocarmycin A and SA DNA Alkylation Reaction," J. Am. Chem. Soc., 1993, 115:9872-9873.

Boger, Dale L. et al., "Synthesis and Preliminary Evaluation of (+)-CBI-Indole$_2$: An Enhanced Functional Analog of (+)-CC-1065," Bioorganic & Medicinal Chemistry Letters, 1991, 1(2):115-120.

Boger, Dale L. et al., "Synthesis and Preliminary Evaluation of Agents Incorporating the Pharmacophore of the Duocarmcin/Pyrindamycin Alkylation Subunit: Identification of the CC-1065/Duocarmycin Common Pharmacophore," 1990, 55:4499-4502.

Boger, Dale L. et al., "Synthesis of N-(tert-Butyloxycarbonyl)-CBI, CBI, CBI-CDPI$_1$, and CBI-CDPI$_2$:Enhanced Functional Analogues of CC-1065 Incorporating the 1,2,9,9a-Tetrahydrocyclopropa[c]benz[e]indol-4-one (CBI) Left-Hand Subunit," 1990, 55:5823-5832.

Boger, Dale L. et al., "Synthesis, Chemical Properties, and Preliminary Evaluation of Substituted CBI Analogs of CC-1065 and the Duocarmycins Incorporating the 7-Cyano-1,2,9,9a-tetrahydrocyclopropa[c]benz[e]indol-4-one Alkylation Subunit: Hammett Quantitation of the Magnitude of Electronic Effects on Functional Reactivity," J. Org. Chem., 1996, 61:4894-4912.

Carl, Philip L. et al., "A Novel Connector Linkage Applicable in Prodrug Design," Journal of Medicinal Chemistry, May 1981 (24)5:479-480.

Chari, Ravi V. J. et al., "Enhancement of the Selectivity and Antitumor Efficacy of a CC-1065 Analogue Through Immunoconjugate Formation," Cancer Res., Sep. 1995, 55:4079-4084.

Chau, Ying et al., "Synthesis and Characterization of Dextran-Peptide-Methotrexate Conjugates for Tumor Targeting via Mediation by Matrix Metalloproteinase II and Matrix Metalloproteinase IX," Bioconjugate Chem., 2004, 15:931-941.

de Groot, Franciscus M. H. et al., "Elongated Multiple Electronic Cascade and Cyclization Spacer Systems in Activatible Anticancer Prodrugs for Enhanced Drug Release," J. Org. Chem., 2001, 66(26):8815-8830.

de Groot, Franciscus M. H. et al., "Synthesis and Biological Evaluation of 2'-Carbamate-Linked and 2'-Carbonate-Linked Prodrugs of Paclitaxel: Selective Activation by the Tumor-Associated Protease Plasmin," Journal of Medicinal Chemistry, 2000, 43(16):3093-3102.

de Groot, Franciscus M. H. et al., "Synthesis and Biological Evaluation of Novel Produgs of Anthracyclins for Selective Activation by the Tumor-Associated Protease Plasmin," 1999, 42(25):5277-5283.

Dubowchik, Gene M. et al., "Cathepsin B-Sensitive Dipeptide Prodrugs. 2. Models of Anticancer Drugs Paclitaxel (Taxol®), Mitomycin C and Doxorubicin," Bioorganic & Medicinal Chemistry Letters, 1998, 8:3347-3352.

Fukuda, Yasumichi et al., "Novel Synthetic of Optically Active CC-1065, U-73,975(Adozelesin), U-80,244(Carzelesin), U-77,779(Bizelesin), KW-2189, and DU-86," Heterocycles, 1997, 45(12):2303-2308.

Hanka, L. J. et al., "CC-1065 (NSC-298223), a New Antitumor Antibiotic: Production, In Vitro Biological Activity, Microbiological Assays and Taxonomy of the Producing Microorganism," The Journal of Antibiotics, Dec. 1978, XXXI(12):1211-1217.

Hurley, Laurence H. et al., "Reaction of the Antitumor Antibiotic CC-1065 with DNA: Structure of a DNA Adduct with DNA Sequence Specificity," Science, Jul. 1984, 226:843-844.

Jonkman-De Vries, J. D. et al., "Systematic Study on the Chemical Stability of the Prodrug Antitumor Agent Carzelesin (U-80,244)," Journal of Pharmaceutical Sciences, Nov. 1996, 85(11):1227-1233.

Kline, Toni et al., "Novel Antitumor Prodrugs Designed for Activation by Matrix Metalloproteinases-2 and -9," Molecular Pharmaceutics, 2004, 1(1):9-22.

Kratz, Felix et al., "Development and In Vitro Efficacy of Novel MMP2 and MMP9 Specific Doxorubicin Albumin Conjugates," Bioorganic & Medicinal Chemistry Letters, 2001, 11:2001-2006.

Li L. H. et al., "Cytotoxicity and Antitumor Activity of Carzelesin, a Prodrug Cyclopropylpyrroloindole Analogue," Cancer Research, Sep. 1992, 52: 4904-4913.

Li, L. H. et al., "CC-1065 (NSC 298223), a Novel Antitumor Agent That Interacts Strongly with Double-stranded DNA," Cancer Research, 1982, 42:999-1004.

Martin, D. G. et al., "Structure of CC-1065 (NSC-298223), a New Antitumor Antibiotic," The Journal of Antibiotics, 1980, 33(8):902-903.

Martin, David G. et al., "CC-1065 (NSC 298223), a Potent New Antitumor Agent Improved Production and Isolation, Characterization and Antitumor Activity," The Journal of Antibiotics, 1981, 34(9):1119-1125.

Nagamura, Satoru et al., "Antitumor Antibiotics: Duocarmycins," Chemistry of Heterocyclic Compounds, 1998, 34(12):1386-1405.

Nagamura, Satoru et al., "Synthesis and Antitumor Activity of Duocarmycin Derivatives," Chem. Pharm. Bull., 1995, 43(9):1530-1535.

Nagamura, Satoru et al., "Synthesis and Antitumor Activity of Duocarmycin Derivatives: Modification of Segment A of Duocarmycin B2," Chem. Pharm. Bull., 1996, 44(9):1723-1730.

Petracek, F. J. et al., "Hydroxymethylketones as Pro-drugs," Annals of New York Academy of Sciences, 1987, 507:353-354.

Sun, Daekyu et al., "Structure-Activity Relationships of (+)-CC-1065 Analogues in the Inhibition of Helicase-Catalyzed Unwinding of Duplex DNA," Journal of Medicinal Chemistry, 1992, 35(10):1773-1782.

Swenson, David H. et al., "Mechanism of Interaction of CC-1065 (NSC 298223) with DNA," Cancer Research, Jul. 1982, 42:2821-2828.

Umemoto, Naoji et al., "Preparation and In Vitro Cytotoxity of a Methotrexate-Anti-MM46 Monoclonal Antibody Conjugate Via an Oligopeptide Spacer," Int. J. Cancer, 1989, 43:677-684.

Warpehoski, M. A. et al., "Stereoelectronic Factors Influencing the Biological Activity and DNA Interaction of Synthetic Antitumor Agents Modeled on CC-1065," Journal of Medicinal Chemistry, 1988, 31: 590-603.

Hay, et al., "Structure-Activity Relationshipf for 4-Nitrobenzyl Carbamates of 5-Aminobenz(e)indoline Minor Groove Alkylating Agents as Prodrugs for GDEPT in Conjunction with *E.coli* Nitroreductase," J. Med. Chem., vol. 46, 2003. pp. 2456-2466.

Wang, et al., "Synthesis and preliminary cytotoxicity study of a cephalosporin-CC-1065 analogue prodrug," Chemical Biology, vol. 1, No. 4, 2001, pp. 1472-1476.

Townes, et al., "Investigation of a Novel Reductively-Activatable Anticancer Prodrug of *SECO*-CBI-TMI, an Analog of Duocarmycin SA," Med Chem Res, vol. 11, No. 4, 2002, pp. 248-253.

Wang, et al., "Synthesis and Preliminary Cytotoxicity Study of Glucuronide Derivatives of CC-1065 Analogues," Bioorganic & Medicinal Chemistry, vol. 11, 2003, pp. 1569-1575.

Tietze, et al., "Highly Selective Glycosylated Prodrugs of Cytostatic CC-1065 Analogues for Antibody-Directed Enzyme Tumor Therapy," Chembiochem, vol. 2, 2001, pp. 758-765.

Hay et al., "Structure-Activity Relationships for 4-Nitrobenzyl Carbamates of 5-Aminobenz[e]indoline Minor Groove Alkylating Agents as Prodrugs for GDEPT in Conjunction with *E. coli* Nitroreductase," J. Med. Chem., vol. 46, 2003, pp. 2456-2466.

\* cited by examiner

US 7,968,586 B2

CYTOTOXIC COMPOUNDS AND CONJUGATES

CROSS REFERENCE TO PRIOR APPLICATIONS

This application is the U.S. national phase of International Application No. PCT/US06/60711, filed Nov. 9, 2006, which claims priority from U.S. Provisional Application No. 60/735,657, filed Nov. 10, 2005. The disclosures of both applications are incorporated herein by reference in their entirety. The International Application published in English on May 24, 2007 as WO 2007/059404 under PCT Article 21(2).

FIELD OF THE INVENTION

The present invention provides cytotoxic compounds, as well as conjugates of the compound with a substrate that can be cleaved in vivo. The conjugates can be used to form prodrugs as other diagnostic and therapeutic moieties.

BACKGROUND OF THE INVENTION

Many therapeutic agents, particularly those that are especially effective in cancer chemotherapy, often exhibit acute toxicity in vivo, especially bone marrow and mucosal toxicity, as well as chronic cardiac and neurological toxicity. Such high toxicity can limit their applications. Development of more and safer specific therapeutic agents, particularly anti-tumor agents, is desirable for greater effectiveness against tumor cells and a decrease in the number and severity of the side effects of these products (toxicity, destruction of non-tumor cells, etc.). Another difficulty with some existing therapeutic agents is their less than optimal stability in plasma. Addition of functional groups to stabilize these compounds resulted in a significant lowering of the activity. Accordingly, it is desirable to identify ways to stabilize compounds while maintaining acceptable therapeutic activity levels.

The search for more selective cytotoxic agents has been extremely active for many decades, the dose limiting toxicity (i.e. the undesirable activity of the cytotoxins on normal tissues) being one of the major causes of failures in cancer therapy. For example, CC-1065 and the duocarmycins are known to be extremely potent cytotoxins.

CC-1065 was first isolated from *Streptomyces zelensis* in 1981 by the Upjohn Company (Hanka et al., *J. Antibiot.* 31: 1211 (1978); Martin et al., *J. Antibiot.* 33: 902 (1980); Martin et al., *J. Antibiot.* 34: 1119 (1981)) and was found to have potent antitumor and antimicrobial activity both in vitro and in experimental animals (Li et al., *Cancer Res.* 42: 999 (1982)). CC-1065 binds to double-stranded B-DNA within the minor groove (Swenson et al., *Cancer Res.* 42: 2821 (1982)) with the sequence preference of 5'-d(A/GNTTA)-3' and 5'-d(AAAAA)-3' and alkylates the N3 position of the 3'-adenine by its CPI left-hand unit present in the molecule (Hurley et al., *Science* 226: 843 (1984)). Despite its potent and broad antitumor activity, CC-1065 cannot be used in humans because it causes delayed death in experimental animals.

Many analogues and derivatives of CC-1065 and the duocarmycins are known in the art. The research into the structure, synthesis and properties of many of the compounds has been reviewed. See, for example, Boger et al., *Angew. Chem. Int. Ed. Engl.* 35: 1438 (1996); and Boger et al., *Chem. Rev.* 97: 787 (1997).

A group at Kyowa Hakko Kogya Co., Ltd. has prepared a number of CC-1065 derivatives. See, for example, U.S. Pat. Nos. 5,101,038; 5,641,780; 5,187,186; 5,070,092; 5,703,080; 5,070,092; 5,641,780; 5,101,038; and 5,084,468; and published PCT application, WO 96/10405 and published European application 0 537 575 A1.

The Upjohn Company (Pharmacia Upjohn) has also been active in preparing derivatives of CC-1065. See, for example, U.S. Pat. Nos. 5,739,350; 4,978,757, 5,332,837 and 4,912,227.

The Scripps Research Institute also has described a variety of derivatives and analogs of CC-1065 and the duocarnycins. See, for example, U.S. Pat. Nos. 5,985,908; 6,060,608; 6,262,271; 6,281,354; 6,310,209; and 6,486,326; and PCT Publication No. WO 97/32850; WO 97/45411; WO 98/52925; WO 99/19298; WO 99/29642 and WO 01/83482. In particular, analogs that incorporate the 1,2,9,9a-tetrahydrocyclopropa[c]benz[e]indole-4-one (CBI) alkylation subunit, referred to as CBI analogs of CC-1065 and the duocarmycins, have been described. See, for example, U.S. Pat. No. 6,548,530 and PCT Publication No. WO 97/12862; WO 03/022806; and WO 04/101767.

Research has also focused on the development of new therapeutic agents which are in the form of prodrugs, compounds that are capable of being converted to drugs (active therapeutic compounds) in vivo by certain chemical or enzymatic modifications of their structure. For purposes of reducing toxicity, this conversion is preferably confined to the site of action or target tissue rather than the circulatory system or non-target tissue. However, even prodrugs are problematic as many are characterized by a low stability in blood and serum, due to the presence of enzymes that degrade or activate the prodrugs before the prodrugs reach the desired sites within the patient's body.

Bristol-Myers Squibb has described particular lysosomal enzyme-cleavable antitumor drug conjugates. See, for example, U.S. Pat. No. 6,214,345. This patent provides an aminobenzyl oxycarbonyl.

Seattle Genetics has published applications U.S. Pat. Appl. 2003/0096743 and U.S. Pat. Appl. 2003/0130189, which describe p-aminobenzylethers in drug delivery agents. The linkers described in these applications are limited to aminobenzyl ether compositions.

Other groups have also described linkers. See for example de Groot et al., *J. Med. Chem.* 42, 5277 (1999); de Groot et al. *J. Org. Chem.* 43, 3093 (2000); de Groot et al., *J. Med. Chem.* 66, 8815, (2001); WO 02/083180; Carl et al., *J. Med. Chem. Lett.* 24, 479, (1981); Dubowchik et al., *Bioorg & Med. Chem. Lett.* 8, 3347 (1998). These linkers include aminobenzyl ether spacer, elongated electronic cascade and cyclization spacer systems, cyclisation eliminations spacers, such as w-amino aminocarbonyls, and a p aminobenzy oxycarbonyl linker.

Stability of cytotoxin drugs, including in vivo stability, is still an important issue that needs to be addressed. In addition, the toxicity of many compounds makes them less useful, so compositions that will reduce drug toxicity, such as the formation of a cleaveable prodrug, are needed. Therefore, in spite of the advances in the art, there continues to be a need for the development of improved therapeutic agents for the treatment of mammals, and humans in particular, more specifically cytotoxins that exhibit high specificity of action, reduced toxicity, and improved stability in blood relative to known compounds of similar structure. The instant invention addresses those needs.

SUMMARY OF THE INVENTION

The present invention relates to cytotoxic compounds useful as drugs or prodrugs and to drug-cleavable substrate conjugates where the drug and cleavable substrate are optionally linked through a self-immolative linker. These conjugates are potent cytotoxins that can be selectively delivered to a site of action of interest in an inactive form and then cleaved to release the active drug. The cleavable substrates of the invention can be cleaved from the cytotoxic drugs by, for example, enzymatic methods in vivo, releasing an active drug moiety from the prodrug derivative.

In one embodiment, the invention is a compound having a structure according to Formula 1:

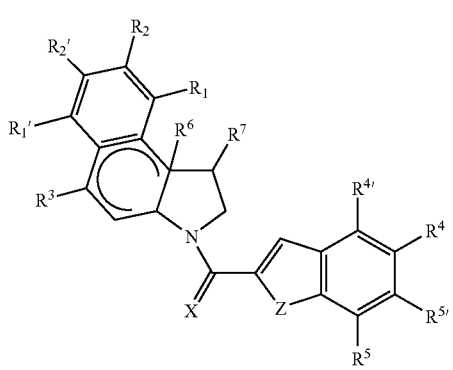

(1)

wherein X and Z are independently selected from O, S and $NR^{23}$ wherein $R^{23}$ is a member selected from H, substituted or unsubstituted alkyl, substituted or unsubstituted heteroalkyl, and acyl;

$R^1$ is H, substituted or unsubstituted lower alkyl, $C(O)R^8$, or $CO_2R^8$, $R^{1'}$ is H, substituted or unsubstituted lower alkyl, or $C(O)R^8$, each $R^8$ is a member independently selected from $NR^9R^{10}$ and $OR^9$ and $R^9$ and $R^{10}$ are members independently selected from H, substituted or unsubstituted alkyl and substituted or unsubstituted heteroalkyl;

$R^2$ is H, substituted or unsubstituted lower alkyl, unsubstituted heteroalkyl, cyano, or alkoxy;

$R^{2'}$ is H, substituted or unsubstituted lower alkyl, or unsubstituted heteroalkyl, $R^3$ is a member selected from the group consisting of $SR^{11}$, $NHR^{11}$ and $OR^{11}$, wherein $R^{11}$ is a member selected from the group consisting of H, substituted alkyl, unsubstituted alkyl, substituted heteroalkyl, unsubstituted heteroalkyl, diphosphates, triphosphates, acyl, $C(O)R^{12}R^{13}$, $C(O)OR^{12}$, $C(O)NR^{12}R^{13}$, $P(O)(OR^{12})_2$, $C(O)CHR^{12}R^{13}$, $SR^{12}$ and $SiR^{12}R^{13}R^{14}$, in which $R^{12}$, $R^{13}$, and $R^{14}$ are members independently selected from H, substituted or unsubstituted alkyl, substituted or unsubstituted heteroalkyl and substituted or unsubstituted aryl, or $R^{12}$ and $R^{13}$ together with the nitrogen or carbon atom to which they are attached are joined to form a substituted or unsubstituted heterocycloalkyl ring system having from 4 to 6 members, optionally containing two or more heteroatoms;

$R^6$ is a single bond which is either present or absent and when present $R^6$ and $R^7$ are joined to form a cyclopropyl ring; and $R^7$ is $CH_2$—$X^1$ or —$CH_2$— joined in said cyclopropyl ring with $R^6$, wherein $X^1$ is a leaving group, $R^4$, $R^{4'}$, $R^5$ and $R^{5'}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$, $OR^{15}$, $CR^{15}$=$NR^{16}$, and $O(CH_2)_nNR^{24}R^{25}$ wherein n is an integer from 1 to 20;

$R^{15}$ and $R^{16}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms;

and $R^{24}$ and $R^{25}$ are independently selected from hydrogen and unsubstituted alkyl, wherein at least one of $R^{24}$ and $R^{25}$ is hydrogen, and wherein at least one of $R^4$, $R^{4'}$, $R^5$ and $R^{5'}$ is $O(CH_2)_n NR^{24}R^{25}$.

In another embodiment, the invention provides a cytotoxic drug-cleavable substrate compound having a structure according to Formula 2:

(2)

The symbol $L^1$ represents a self-immolative spacer where m is an integer of 0, 1, 2, 3, 4, 5, or 6.

The symbol $X^2$ represents a cleavable substrate, preferably, an enzyme cleavable substrate.

The symbol D is a drug having the following formula:

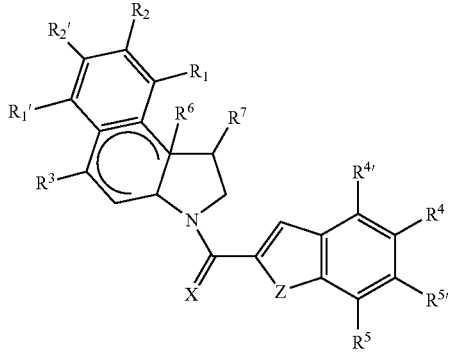

wherein X and Z are independently selected from O, S and $NR^{23}$ wherein $R^{23}$ is a member selected from H, substituted or unsubstituted alkyl, substituted or unsubstituted heteroalkyl, and acyl;

$R^1$ is H, substituted or unsubstituted lower alkyl, $C(O)R^8$, or $CO_2R^8$, $R^{1'}$ is H, substituted or unsubstituted lower alkyl, or $C(O)R^8$, each $R^8$ is a member independently selected from $NR^9R^{10}$ and $OR^9$ and $R^9$ and $R^{10}$ are members independently selected from H, substituted or unsubstituted alkyl and substituted or unsubstituted heteroalkyl;

$R^2$ is H, substituted or unsubstituted lower alkyl, unsubstituted heteroalkyl, cyano, or alkoxy;

$R^{2'}$ is H, substituted or unsubstituted lower alkyl, or unsubstituted heteroalkyl, $R^3$ is a member selected from the group consisting of $SR^{11}$, $NHR^{11}$ and $OR^{11}$, wherein $R^{11}$ is a member selected from the group consisting of H, substituted alkyl, unsubstituted alkyl, substituted heteroalkyl, unsubstituted heteroalkyl, diphosphates, triphosphates, acyl, $C(O)R^{12}R^{13}$, $C(O)OR^{12}$, $C(O)NR^{12}R^{13}$, $P(O)(OR^{12})_2$, $C(O)CHR^{12}R^{13}$, $SR^{12}$ and $SiR^{12}R^{13}R^{14}$, $R^{12}$, $R^{13}$, and $R^{14}$ are members independently selected from H, substituted or unsubstituted alkyl, substituted or unsubstituted heteroalkyl and substituted or unsubstituted aryl, or $R^{12}$ and $R^{13}$ together with the nitrogen or carbon atom to which they are attached are joined to form a substituted or unsubstituted heterocycloalkyl ring system having from 4 to 6 members, optionally containing two or more heteroatoms;

$R^6$ is a single bond which is either present or absent and when present $R^6$ and $R^7$ are joined to form a cyclopropyl ring; and $R^7$ is $CH_2$—$X^1$ or —$CH_2$— joined in said cyclopropyl ring with $R^6$, wherein $X^1$ is a leaving group, $R^4$, $R^{4'}$, $R^5$ and $R^{5'}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, $NO_2$, $NR^{15}R^{16}$, $NC(O)R^5$, $OC(O)NR^{15}R^{16}$, $OC(O)OR^{15}$, $C(O)R^{15}$, $SR^{15}$, $OR^{15}$, $CR$=$NR^{16}$, and $O(CH_2)_nNR^{24}R^{25}$ wherein n is an integer from 1 to 20;

$R^{15}$ and $R^{16}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms;

and $R^{24}$ and $R^{25}$ are independently selected from hydrogen and unsubstituted alkyl, wherein at least one of $R^{24}$ and $R^{25}$ is hydrogen, and wherein at least one of $R^4$, $R^{4'}$, $R^5$ and $R^{5'}$ is $O(CH_2)_n NR^{24}R^{25}$ and wherein at least one of $R^{11}$, $R^{12}$, $R^{13}$, $R^{15}$ or $R^{16}$ links said drug to $L^1$, if present, or to $X^2$.

In yet another aspect, the invention pertains to pharmaceutical formulations. Such formulations typically comprise a cytotoxic compound or a conjugate of the cytotoxic compound of the invention and a pharmaceutically acceptable carrier.

In still a further aspect, the invention pertains to methods of using the cytotoxic compound or a conjugate of the cytotoxic compound of the invention. For example, the invention provides a method of killing a cell, wherein a conjugate compound of the invention is administered to the cell an amount sufficient to kill the cell. In a preferred embodiment, the cell is a tumor cell. In another embodiment, the invention provides a method of retarding or stopping the growth of a tumor in a mammalian subject, wherein a conjugate compound of the invention is administered to the subject an amount sufficient to retard or stop growth of the tumor.

Other aspects, advantages and objects of the invention will be apparent from review of the detailed description below.

DETAILED DESCRIPTION OF THE INVENTION

Abbreviations
As used herein, "Ala," refers to alanine.
"Boc," refers to t-butyloxycarbonyl.
"CPI," refers to cyclopropapyrroloindole.
"Cbz," is carbobenzoxy.
As used herein, "DCM," refers to dichloromethane.
"DDQ," refers to 2,3-dichloro-5,6-dicyano-1,4-benzoquinone.
DIPEA is diisopropylethalamine
"DMDA" is N,N'-dimethylethylene diamine
"RBF" is a round bottom flask
"DMF" is N,B-dimethylformamide
"HATU" is N-[[(dimethylamino)-1H-1,2,3-triazolo[4,5-b]pyridin-1yl]methylene]-N-methylmethanaminium hexafluorophosphate N-oxide
As used herein, the symbol "E," represents an enzymatically cleaveable group.
"EDCI" is 1-(3-dimethylaminopropyl)-3-ethylcarbodiimide.
As used herein, "FMOC," refers to 9-fluorenylmethyloxycarbonyl.
"FMOC" refers to 9-fluorenylmethoxycarbonyl.
"HOAt" is 7-Aza-1-hydroxybenzotriazole.
"Leu" is leucine.
"PABA" refers to para-aminobenzoic acid.
PEG refers to polyethylene glycol
"PMB," refers to para-methoxybenzyl.
"TBAF," refers to tetrabutylammonium fluoride.
The abbreviation "TBSO," refers to t-butyldimethylsilyl ether.
As used herein, "TEA," refers to triethylamine.
"TFA," refers to trifluororoacetic acid.
The symbol "Q" refers to a therapeutic agent, diagnostic agent or detectable label.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

The term "therapeutic agent" is intended to mean a compound that, when present in a therapeutically effective amount, produces a desired therapeutic effect on a mammal. For treating carcinomas, it is desirable that the therapeutic agent also be capable of entering the target cell.

The term "cytotoxin" is intended to mean a therapeutic agent having the desired effect of being cytotoxic to cancer cells. Cytotoxic means that the agent arrests the growth of, or kills the cells. Exemplary cytotoxins include, by way of example and not limitation, combretastatins, duocarmycins, the CC-1065 anti-tumor antibiotics, anthracyclines, and related compounds. Other cytotoxins include mycotoxins, ricin and its analogues, calicheamycins, doxirubicin and maytansinoids.

The term "prodrug" and the terms "drug conjugate" and "drug-cleavable substrate conjugate" are used herein interchangeably. Both refer to a compound that is relatively innocuous to cells while still in the conjugated form but which is selectively degraded to a pharmacologically active form by conditions, e.g., enzymes, located within or in the proximity of target cells.

The term "marker" is intended to mean a compound useful in the characterization of tumors or other medical condition, for example, diagnosis, progression of a tumor, and assay of the factors secreted by tumor cells. Markers are considered a subset of "diagnostic agents."

The term "selective" as used in connection with enzymatic cleavage means that the rate of rate of cleavage of the linker moiety is greater than the rate of cleavage of a peptide having a random sequence of amino acids.

The term "self-immolative spacer" refers to a bifunctional chemical moiety that is capable of covalently linking two chemical moieties into a normally stable tripartate molecule. The self-immolative spacer is capable of spontaneously separating from the second moiety if the bond to the first moiety is cleaved.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. These terms also encompass the term "antibody."

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. One amino acid that may be used in particular is citrulline, which is a precursor to arginine and is involved in the formation of urea in the liver. Amino acid mimetics refers to chemical compounds that have a structure that is different from the general chemical structure of an amino acid, but functions in a manner similar to a naturally occurring amino acid. The term "unnatural amino acid" is intended to represent the "D" stereochemical form of the twenty naturally occurring amino acids described above. It is further understood that the term unnatural amino acid includes homologues of the natural amino acids, and synthetically modified forms of the natural amino acids. The synthetically modified forms include, but are not limited to, amino acids having alkylene chains shortened or lengthened by up to two carbon atoms, amino acids comprising optionally substituted aryl groups, and amino acids comprised halogenated groups, preferably halogenated alkyl and aryl groups. When attached to a linker or conjugate of the invention, the amino acid is in the form of an "amino acid side chain", where the carboxylic acid group of the amino acid has been replaced with a keto (C(O)) group. Thus, for example, an alanine side chain is —C(O)—CH(NH$_2$)—CH$_3$, and so forth.

Amino acids and peptides may be protected by blocking groups. A blocking group is an atom or a chemical moiety that protects the N-terminus of an amino acid or a peptide from undesired reactions and can be used during the synthesis of a drug-cleavable substrate conjugate. It should remain attached to the N-terminus throughout the synthesis, and may be removed after completion of synthesis of the drug conjugate by chemical or other conditions that selectively achieve its removal. The blocking groups suitable for N-terminus protection are well known in the art of peptide chemistry. Exemplary blocking groups include, but are not limited to, hydrogen, D-amino acid, and carbobenzoxy (Cbz) chloride.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260: 2605-2608 (1985); Rossolini et al., *Mol. Cell. Probes* 8: 91-98 (1994)). The term nucleic acid is used interchangeably with gene, cDNA, mRNA, oligonucleotide, and polynucleotide.

The symbol ⌇, whether utilized as a bond or displayed perpendicular to a bond indicates the point at which the displayed moiety is attached to the remainder of the molecule, solid support, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "alkylene" by itself or as part of another substituent means a divalent radical derived from an alkane, as exemplified, but not limited, by —CH$_2$CH$_2$CH$_2$CH$_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen, carbon and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). The terms "heteroalkyl" and "heteroalkylene" encompass poly(ethylene glycol) and its derivatives (see, for example, Shearwater Polymers Catalog, 2001). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The term "lower" in combination with the terms "alkyl" or "heteroalkyl" refers to a moiety having from 1 to 6 carbon atoms.

The terms "alkoxy," "alkylamino," "alkylsulfonyl," and "alkylthio" (or thioalkoxy) are used in their conventional sense, and refer to those alkyl groups attached to the remainder of the molecule via an oxygen atom, an amino group, an $SO_2$ group or a sulfur atom, respectively. The term "arylsulfonyl" refers to an aryl group attached to the remainder of the molecule via an $SO_2$ group, and the term "sulfhydryl" refers to an SH group.

In general, an "acyl substituent" is also selected from the group set forth above. As used herein, the term "acyl substituent" refers to groups attached to, and fulfilling the valence of a carbonyl carbon that is either directly or indirectly attached to the polycyclic nucleus of the compounds of the present invention.

The terms "cycloalkyl" and "heterocycloalkyl", by themselves or in combination with other terms, represent, unless otherwise stated, cyclic versions of substituted or unsubstituted "alkyl" and substituted or unsubstituted "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The heteroatoms and carbon atoms of the cyclic structures are optionally oxidized.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a substituted or unsubstituted polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen, carbon and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Aryl" and "heteroaryl" also encompass ring systems in which one or more non-aromatic ring systems are fused, or otherwise bound, to an aryl or heteroaryl system.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroalkyl substituents," respectively, and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, the aryl substituents and heteroaryl substituents are generally referred to as "aryl substituents" and "heteroaryl substituents," respectively and are varied and selected from, for example: halogen, —OR', =O, =NR', =N—OR', —NR'R", —SR', -halogen, —SiR'R"R''', —OC(O)R', —C(O)R', —CO$_2$R', —CONR'R", —O—OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R''' and R'''' are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R''' and R'''' groups when more than one of these groups is present.

Two of the aryl substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$) alkyl.

As used herein, the term "diphosphate" includes but is not limited to an ester of phosphoric acid containing two phosphate groups. The term "triphosphate" includes but is not limited to an ester of phosphoric acid containing three phosphate groups. For example, particular drugs having a diphosphate or a triphosphate include:

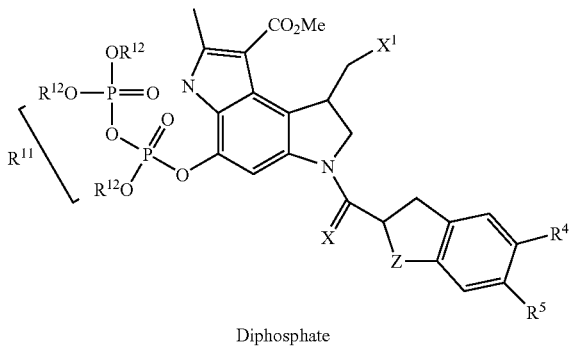

Diphosphate

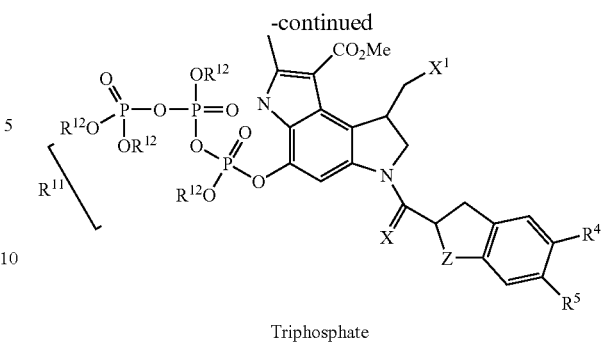

Triphosphate

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups.

The term "pharmaceutically acceptable carrier", as used herein means a pharmaceutically-acceptable material, composition or vehicle, such as a liquid or solid filler, diluent, excipient, solvent or encapsulating material, involved in carrying or transporting a chemical agent. Pharmaceutically acceptable carriers include pharmaceutically acceptable salts, where the term "pharmaceutically acceptable salts" includes salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

As used herein, the term "leaving group" refers to a portion of a substrate that is cleaved from the substrate in a reaction.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains interconnected by disulfide bonds, or an antigen binding portion thereof. Each heavy chain is comprised of a heavy chain variable region ($V_H$) and a heavy chain constant region. The heavy chain constant region is comprised of three domains, $C_{H1}$, $C_{H2}$ and $C_{H3}$, and may be of the mu, delta, gamma, alpha or epsilon isotype. Each light chain is comprised of a light chain variable region ($V_L$) and a light chain constant region. The light chain constant region is comprised of one domain, $C_L$, which may be of the kappa or lambda isotype. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The terms "antibody fragment" or "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antibody fragment" or "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The terms "monoclonal antibody" as used herein refers to a preparation of antibody molecules of single molecular composition. A monoclonal antibody composition displays a single binding specificity and affinity for a particular epitope.

"Solid support," as used herein refers to a material that is substantially insoluble in a selected solvent system, or which can be readily separated (e.g., by precipitation) from a selected solvent system in which it is soluble. Solid supports useful in practicing the present invention can include groups that are activated or capable of activation to allow selected species to be bound to the solid support. A solid support can also be a substrate, for example, a chip, wafer or well, onto which an individual, or more than one compound, of the invention is bound.

"Reactive functional group," as used herein refers to groups including, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like (see, for example, Hermanson, BIOCONJUGATE TECHNIQUES, Academic press, San Diego, 1996). Methods to prepare each of these functional groups are well known in the art and their application to or modification for a particular purpose is within the ability of one of skill in the art (see, for example, Sandler and Karo, eds. ORGANIC FUNCTIONAL GROUP PREPARATIONS, Academic Press, San Diego, 1989). The reactive functional groups may be protected or unprotected.

The compounds of the invention are prepared as a single isomer (e.g., enantiomer, cis-trans, positional, diastereomer) or as a mixture of isomers. In a preferred embodiment, the compounds are prepared as substantially a single isomer.

Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.) VOGEL's ENCYCLOPEDIA OF PRACTICAL ORGANIC CHEMISTRY 5$^{TH}$ ED., Longman Scientific and Technical Ltd., Essex, 1991, pp. 809-816; and Heller, Acc. Chem. Res. 23: 128 (1990).

CBI Analogues

The compounds described herein are generally CBI analogues in that they incorporate the 1,2,9,9a-tetrahydrocyclopropa[c]benz[e]indole-4-one (CBI) alkylating domain or alkylation subunit. The compounds may be used as drugs. Preferred drugs of the current invention include cytotoxic drugs useful in cancer therapy. Cytotoxic drugs useful in the current invention include, for example, CBI (1,2,9,9a-tetrahydrocyclopropa[c]benz[e]indol-4-one)-based analogues, MCBI (7-methoxy-1,2,9,9a-tetra-hydrocyclopropa[c]benz[e]indol-4-one)-based analogues and CCBI (7-cyano-1,2,9,9a-tetra-hydrocyclo-propa[c]benz[e]-indol-4-one)-based analogues.

In one embodiment, a compound of the invention has the following formula (I):

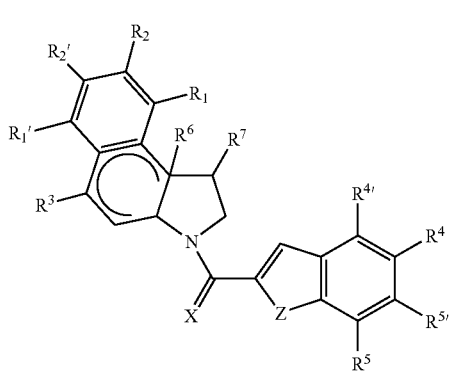

(1)

wherein X and Z are independently selected from O, S and $NR^{23}$ wherein $R^{23}$ is a member selected from H, substituted or unsubstituted alkyl, substituted or unsubstituted heteroalkyl, and acyl;

$R^1$ is H, substituted or unsubstituted lower alkyl, $C(O)R^8$, or $CO_2R^8$, $R^{1'}$ is H, substituted or unsubstituted lower alkyl, or $C(O)R^8$, each $R^8$ is a member independently selected from $NR^9R^{10}$ and $OR^9$ and $R^9$ and $R^{10}$ are members independently selected from H, substituted or unsubstituted alkyl and substituted or unsubstituted heteroalkyl;

$R^2$ is H, substituted or unsubstituted lower alkyl, unsubstituted heteroalkyl, cyano, or alkoxy;

$R^{2'}$ is H, substituted or unsubstituted lower alkyl, or unsubstituted heteroalkyl, $R^3$ is a member selected from the group consisting of $SR^{11}$, $NHR^{11}$ and $OR^{11}$, wherein $R^{11}$ is a member selected from the group consisting of H, substituted alkyl, unsubstituted alkyl, substituted heteroalkyl, unsubstituted heteroalkyl, diphosphates, triphosphates, acyl, $C(O)R^{12}R^{13}$, $C(O)OR^{12}$, $C(O)NR^{12}R^{13}$, $P(O)(OR^{12})_2$, $C(O)CHR^{12}R^{13}$, $SR^{12}$ and $SiR^{12}R^{13}R^{14}$, in which $R^{12}$, $R^{13}$, and $R^{14}$ are members independently selected from H, substituted or unsubstituted alkyl, substituted or unsubstituted heteroalkyl and substituted or unsubstituted aryl, or $R^{12}$ and $R^{13}$ together with the nitrogen or carbon atom to which they are attached are joined to form a substituted or unsubstituted heterocycloalkyl ring system having from 4 to 6 members, optionally containing two or more heteroatoms;

$R^6$ is a single bond which is either present or absent and when present $R^6$ and $R^7$ are joined to form a cyclopropyl ring; and $R^7$ is $CH_2$—$X^1$ or —$CH_2$— joined in said cyclopropyl ring with $R^6$, wherein $X^1$ is a leaving group, $R^4$, $R^{4'}$, $R^5$ and $R^{5'}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$, $OR^{15}$, $CR$=$NR^{16}$, and $O(CH_2)_nNR^{24}R^{25}$ wherein n is an integer from 1 to 20, preferably, n is an integer from 2 to 6;

$R^{15}$ and $R^{16}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms;

and $R^{24}$ and $R^{25}$ are independently selected from hydrogen and unsubstituted alkyl, wherein at least one of $R^{24}$ and $R^{25}$ is hydrogen, and wherein at least one of $R^4$, $R^{4'}$, $R^5$ and $R^{5'}$ is $O(CH_2)_nNR^{24}R^{25}$.

U.S. patent application Ser. Nos. 11/134,685 and 11/134,826 and U.S. Provisional Patent Application Ser. Nos. 60/572,667; 60/661,174; and 60/669,871 are all herein incorporated by reference.

As discussed above, $X^1$ may be a leaving group. Useful leaving groups include, but are not limited to, halogens, azides, sulfonic esters (e.g., alkylsulfonyl, arylsulfonyl), oxonium ions, alkyl perchlorates, ammonioalkanesulfonate esters, alkylfluorosulfonates and fluorinated compounds (e.g., triflates, nonaflates, tresylates) and the like. Particular halogens useful as leaving groups are F, Cl and Br. The choice of these and other leaving groups appropriate for a particular set of reaction conditions is within the abilities of those of skill in the art (see, for example, March J, ADVANCED ORGANIC CHEMISTRY, 2nd Edition, John Wiley and Sons, 1992; Sandler S R, Karo W, ORGANIC FUNCTIONAL GROUP PREPARATIONS, 2nd Edition, Academic Press, Inc., 1983; and Wade L G, COMPENDIUM OF ORGANIC SYNTHETIC METHODS, John Wiley and Sons, 1980).

In some embodiments, $R^4$, $R^{4'}$, $R^5$, and $R^{5'}$ are members independently selected from H, halogen, $NH_2$, OMe, $O(CH_2)_2N(Me)_2$ and $NO_2$. In some embodiments, at least one of $R^4$, $R^{4'}$, $R^5$, and $R^{5'}$ is $O(CH_2)_2N(Me)_2$. In some embodiments, one of $R^4$, $R^{4'}$, $R^5$ or $R^{5'}$ is $O(CH_2)_2N(Me)_2$ and the others of $R^4$, $R^{4'}$, $R^5$ and $R^{5'}$ are H. In other embodiments, $R^4$ is $O(CH_2)_2N(Me)_2$ and $R^{4'}$, $R^5$ and $R^{5'}$ are H.

In some embodiments, $R^7$ is $CH_2$—$X^1$ where $X^1$ is F, Cl or Br and $R^6$ is absent. In some embodiments, the drug is selected such that the leaving group $X^1$ is a member selected from the group consisting of halogen, alkylsulfonyl, arylsulfonyl, and azide. In some embodiments, $X^1$ is Cl or Br.

In some embodiments, Z is O. In some embodiments, X and Z are O.

In some embodiments, $R^2$ is H, methyl, or cyano and $R^1$, $R^{1'}$, and $R^{2'}$ are H. In some embodiments, $R^1$, $R^{1'}$, $R^2$, and $R^{2'}$ are H. In some embodiments, $R^1$, $R^{1'}$, and $R^{2'}$ are H.

In some embodiments, $R^3$ is a reactive group as described below.

In at least some embodiments, $R^{24}$ and $R^{25}$ are hydrogen.

A preferred formula for drug, $D^1$, is the following:

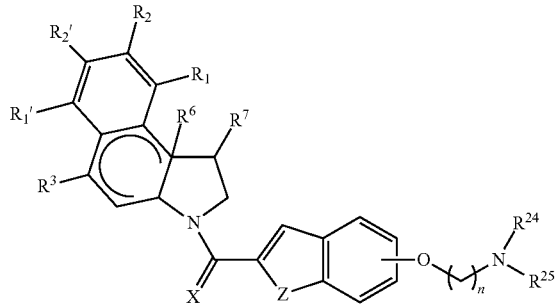

Another preferred embodiment of drug $D^1$ is the following:

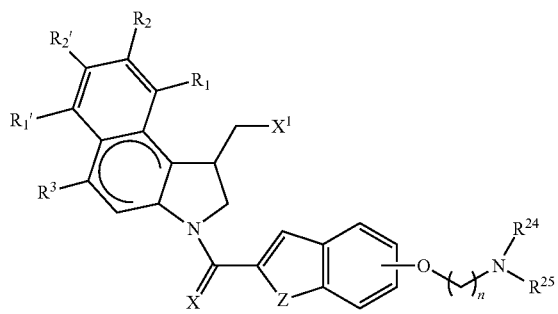

Yet additional preferred embodiments of drug $D^1$ are the following:

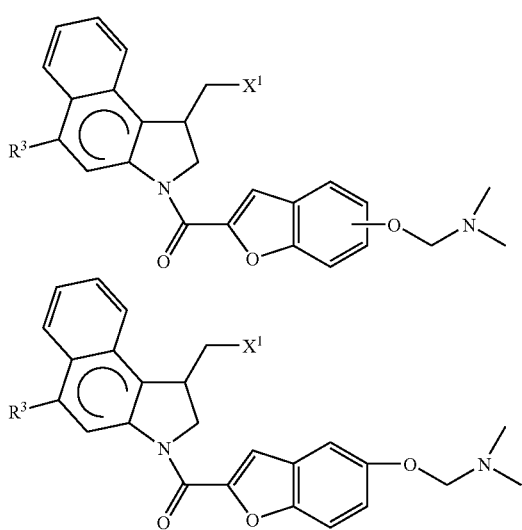

-continued

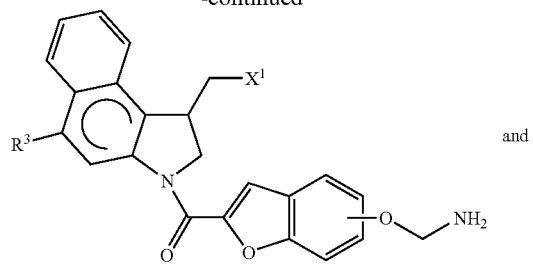

and

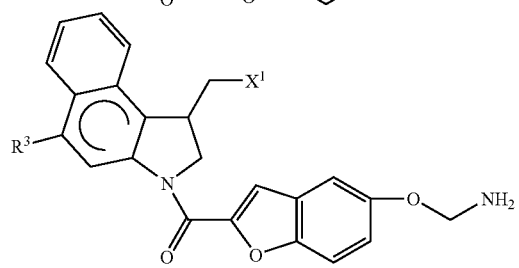

Drug-Cleavable Substrate Conjugates

The drugs, depicted as "D" herein, can be provided in the current invention as part of a drug-cleavable substrate conjugate where the drug is linked to a cleavable substrate, $X^2$, optionally via a self-immolative linker, $L^1$. This conjugate can be a prodrug. The drug typically possesses a desired biological activity and contains a reactive functional group to link to the cleavable substrate. The desired biological activity includes the diagnosis, cure, mitigation, treatment, or prevention of disease in an animal such as a human. Preferred reactive functional groups include primary or secondary amines, hydroxyls, sulfhydryls, carboxyls, aldehydes, and ketones. More preferred reactive functional groups include hydroxyls, primary or secondary amines, sulfhydryls and carboxylic acid functional groups. Even more preferred reactive functional groups include hydroxyls, primary and secondary amines and carboxylic acid functional groups. The drug typically has at least one, but may have 2, 3, 4, 5, 6 or more reactive functional groups.

The drug-cleavable substrate conjugate is effective for the usual purposes for which the corresponding drugs are effective, but may have superior efficacy because of the ability to transport the drug to the desired cell (e.g., a tumor cell) where it is of particular benefit. For example, the drug may be selected to be activated at a site of tumor cells by conjugation to a tumor-specific cleavable substrate. These tumor specific drug-cleavable substrate conjugates have tumor specificity arising from the specificity of the cleavable substrate. The specificity can arise when the cleavable substrate is preferentially cleaved in or around the tumor cells. Examples include conjugates that are highly selective substrates for tumor specific enzymes or enzymes which are associated, naturally or artificially, with the tumor. These enzymes are present in the proximity of the tumor in sufficient amounts to generate cytotoxic levels of free drug in the vicinity of the tumor.

In another approach, referred to as antibody-directed enzyme prodrug therapy (ADEPT), an enzyme is attached to an antibody specific for a tumor antigen, to thereby direct the enzyme to the site of tumor cells. The drug is then conjugated to a substrate cleavable by the enzyme attached to the tumor-specific antibody. Thus, these drug-cleavable substrate conjugates have tumor specificity arising from the localization of the enzyme at the site of tumor cells through the attachment of the enzyme to the tumor-specific antibody.

One advantage of the drug-cleavable substrate complex is that they can be less toxic than the corresponding free drug; additionally, the specificity of the complex may allow for lower overall concentrations to be used relative to the free drug since the increased specificity will result in a higher percentage of the complex to be present at the tumor site.

In one embodiment, the invention provides a cytotoxic drug-cleavable substrate compound having a structure according to Formulas 2:

$$X^2-(L^1)_m-D \quad (2)$$

The symbol $L^1$ represents a self-immolative spacer where m is an integer of 0, 1, 2, 3, 4, 5, or 6. Preferably, M is 0, 1, or 2.

The symbol $X^2$ represents a cleavable substrate, preferably, an enzyme cleavable substrate.

The symbol D is a drug having the following formula:

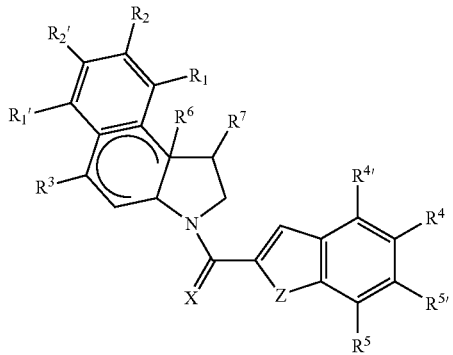

wherein X and Z are independently selected from O, S and $NR^{23}$ wherein $R^{23}$ is a member selected from H, substituted or unsubstituted alkyl, substituted or unsubstituted heteroalkyl, and acyl;

$R^1$ is H, substituted or unsubstituted lower alkyl, $C(O)R^8$, or $CO_2R^8$, $R^{1'}$ is H, substituted or unsubstituted lower alkyl, or $C(O)R^8$, each $R^8$ is a member independently selected from $NR^9R^{10}$ and $OR^9$ and $R^9$ and $R^{10}$ are members independently selected from H, substituted or unsubstituted alkyl and substituted or unsubstituted heteroalkyl;

$R^2$ is H, substituted or unsubstituted lower alkyl, unsubstituted heteroalkyl, cyano, or alkoxy;

$R^{2'}$ is H, substituted or unsubstituted lower alkyl, or unsubstituted heteroalkyl, $R^3$ is a member selected from the group consisting of $SR^{11}$, $NHR^{11}$ and $OR^{11}$, wherein $R^{11}$ is a member selected from the group consisting of H, substituted alkyl, unsubstituted alkyl, substituted heteroalkyl, unsubstituted heteroalkyl, diphosphates, triphosphates, acyl, $C(O)R^{12}R^{13}$, $C(O)OR^{12}$, $C(O)NR^{12}R^{13}$, $P(O)(OR^{12})_2$, $C(O)CHR^{12}R^{13}$, $SR^{12}$ and $SiR^{12}R^{13}R^{14}$, in which $R^{12}$, $R^{13}$, and $R^{14}$ are members independently selected from H, substituted or unsubstituted alkyl, substituted or unsubstituted heteroalkyl and substituted or unsubstituted aryl, or $R^{12}$ and $R^{13}$ together with the nitrogen or carbon atom to which they are attached are joined to form a substituted or unsubstituted heterocycloalkyl ring system having from 4 to 6 members, optionally containing two or more heteroatoms;

$R^6$ is a single bond which is either present or absent and when present $R^6$ and $R^7$ are joined to form a cyclopropyl ring; and $R^7$ is $CH_2-X^1$ or $-CH_2-$ joined in said cyclopropyl ring with $R^6$, wherein $X^1$ is a leaving group, $R^4$, $R^{4'}$, $R^5$ and $R^{5'}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$, $OR^{15}$, $CR^{15}=NR^{16}$, and $O(CH_2)_nNR^{21}R^{25}$ wherein n is an integer from 1 to 20;

$R^{15}$ and $R^{16}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms;

and $R^{24}$ and $R^{25}$ are independently selected from hydrogen and unsubstituted alkyl, wherein at least one of $R^{24}$ and $R^{25}$ is hydrogen, and wherein at least one of $R^4$, $R^{4'}$, $R^5$ and $R^{5'}$ is $O(CH_2)_n NR^{24}R^{25}$ and wherein at least one of $R^{11}$, $R^{12}$, $R^{13}$, $R^{15}$ or $R^{16}$ links said drug to $L^1$, if present, or to $X^2$.

Any of the drugs described in the preceding section can be used.

Cleavable Substrate

The cleavable substrates of the current invention are depicted as "$X^2$". Preferably, the cleavable substrate is a cleavable enzyme substrate that can be cleaved by an enzyme. Preferably, the enzyme is preferentially associated, directly or indirectly, with the tumor or other test cells to be treated. The enzyme may be generated by the tumor or other test cells to be treated. For example, the cleavable substrate can be a peptide that is preferentially cleavable by an enzyme found around or in a tumor or other target cell. Additionally or alternatively, the enzyme can be attached to a targeting agent that binds specifically to tumor cells, such as an antibody specific for a tumor antigen.

As examples of enzyme cleavable substrates suitable for coupling to the drugs described above, PCT Patent Applications Publication Nos. WO 00/33888, WO 01/95943, WO 01/95945, WO 02/00263, and WO 02/100353, all of which are incorporated herein by reference, disclose attachment of a cleavable peptide to a drug. The peptide is cleavable by an enzyme, such as a trouase (such as thimet oligopeptidase), CD10 (neprilysin), a matrix metalloprotease (such as MMP2 or MMP9), a type II transmembrane serine protease (such as Hepsin, testisin, TMPRSS4, or matritriptase/MT-SP1), or a cathepsin, associated with a tumor. In this embodiment, a prodrug includes the drug as described above, a peptide, a stabilizing group, and optionally a linking group between the drug and the peptide. The stabilizing group is attached to the end of the peptide to protect the prodrug from degradation before arriving at the tumor or other target cell. Examples of suitable stabilizing groups include non-amino acids, such as succinic acid, diglycolic acid, maleic acid, polyethylene glycol, pyroglutamic acid, acetic acid, naphthylcarboxylic acid, terephthalic acid, and glutaric acid derivatives; as well as non-genetically-coded amino acids or aspartic acid or glutamic acid attached to the N-terminus of the peptide at the β-carboxy group of aspartic acid or the γ-carboxyl group of glutamic acid.

The peptide typically includes 3-12 (or more) amino acids. The selection of particular amino acids will depend, at least in part, on the enzyme to be used for cleaving the peptide, as well as, the stability of the peptide in vivo. One example of a suitable cleavable peptide is βAlaLeuAlaLeu [SEQ. ID NO. 1]. This can be combined with a stabilizing group to form succinyl-βAlaLeuAlaLeu. Other examples of suitable cleavable peptides are provided in the references cited above.

As one illustrative example, CD10, also known as neprilysin, neutral endopeptidase (NEP), and common acute lymphoblastic leukemia antigen (CALLA), is a type II cell-surface zinc-dependent metalloprotease. Cleavable substrates suitable for use with CD10 include LeuAlaLeu and IleAlaLeu. Other known substrates for CD10 include peptides of up to 50 amino acids in length, although catalytic efficiency often declines as the substrate gets larger.

Another illustrative example is based on matrix metalloproteases (MMP). Probably the best characterized proteolytic enzymes associated with tumors, there is a clear correlation of activation of MMPs within tumor microenvironments. In particular, the soluble matrix enzymes MMP2 (gelatinase A) and MMP9 (gelatinase B), have been intensively studied, and shown to be selectively activated during tissue remodeling including tumor growth. Peptide sequences designed to be cleaved by MMP2 and MMP9 have been designed and tested for conjugates of dextran and methotrexate (Chau et al., *Bioconjugate Chem.* 15:931-941 (2004)); PEG (polyethylene glycol) and doxorubicin (Bae et al., *Drugs Exp. Clin. Res.* 29:15-23 (2004)); and albumin and doxorubicin (Kratz et al., *Bioorg. Med. Chem. Lett.* 11:2001-2006 (2001)). Examples of suitable sequences for use with MMPs include, but are not limited to, ProValGlyLeuIleGly [SEQ. ID NO. 2], GlyProLeuGlyVal [SEQ. ID NO. 3], GlyProLeuGlyIleAlaGlyGln [SEQ. ID NO. 4], ProLeuGlyLeu [SEQ. ID NO. 5], GlyProLeuGlyMetLeuSerGln [SEQ. ID NO. 6], and GlyProLeuGlyLeuTrpAlaGln [SEQ. ID NO. 7]. (See, e.g., the previously cited references as well as Kline et al., *Mol. Pharmaceut.* 1:9-22 (2004) and Liu et al., *Cancer Res.* 60:6061-6067 (2000).) Other cleavable substrates can also be used.

Yet another example is type II transmembrane serine proteases. This group of enzymes includes, for example, hepsin, testisin, and TMPRSS4. GlnAlaArg is one substrate sequence that is useful with matritriptase/MT-SP1 (which is over-expressed in breast and ovarian cancers) and LeuSerArg is useful with hepsin (over-expressed in prostate and some other tumor types). (See, e.g., Lee et. al., *J. Biol. Chem.* 275:36720-36725 and Kurachi and Yamamoto, *Handbook of Proeolytic Enzymes* Vol. 2, $2^{nd}$ edition (Barrett A J, Rawlings N D & Woessner J F, eds) pp. 1699-1702 (2004).) Other cleavable substrates can also be used.

Another type of cleavable substrate arrangement includes preparing a separate enzyme capable of cleaving the cleavable substrate that becomes associated with the tumor or cells. For example, an enzyme can be coupled to a tumor-specific antibody (or other entity that is preferentially attracted to the tumor or other target cell such as a receptor ligand) and then the enzyme-antibody conjugate can be provided to the patient. The enzyme-antibody conjugate is directed to, and binds to, antigen associated with the tumor. Subsequently, the drug-cleavable substrate conjugate is provided to the patient as a prodrug. The drug is only released in the vicinity of the tumor when the drug-cleavable substrate conjugate interacts with the enzyme that has become associated with the tumor so that the cleavable substrate is cleaved and the drug is freed. For example, U.S. Pat. Nos. 4,975,278; 5,587,161; 5,660,829; 5,773,435; and 6,132,722, all of which are incorporated herein by reference, disclose such an arrangement. Examples of suitable enzymes and substrates include, but are not limited to, β-lactamase and cephalosporin derivatives, carboxypeptidase G2 and glutamic and aspartic folate derivatives.

In one embodiment, the enzyme-antibody conjugate includes an antibody, or antibody fragment, that is selected based on its specificity for an antigen expressed on a target cell, or at a target site, of interest. A wide variety of tumor-specific or other disease-specific antigens have been identified and antibodies to those antigens have been used or proposed for use in the treatment of such tumors or other diseases. The antibodies that are known in the art can be used in the conjugates of the invention, in particular for the treatment of the disease with which the target antigen is associated. Non-limiting examples of target antigens (and their associated diseases) to which an antibody-linker-drug conjugate of the invention can be targeted include: Her2 (breast cancer), CD20 (lymphomas), EGFR (solid tumors), CD22 (lymphomas, including non-Hodgkin's lymphoma), CD52 (chronic lymphocytic leukemia), CD33 (acute myelogenous leukemia), CD4 (lymphomas, autoimmune diseases, including rheumatoid arthritis), CD30 (lymphomas, including non-Hodgkin's lymphoma), Muc18 (melanoma), integrins (solid tumors), PSMA (prostate cancer, benign prostatic hyperplasia), CEA (colorectal cancer), CD11a (psoriasis), CD80 (psoriasis), CD23 (asthma), CD40L (immune thrombobcytopenic purpura), CTLA4 (T cell lymphomas) and BLys (autoimmune diseases, including systemic lupus erythematosus).

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in MONOCLONAL ANTIBODIES AND CANCER THERAPY, Alan R. Liss, Inc. (1985)).

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired.

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6: 511-519 (1976)). Alternative methods of immortalization include transformation with Epstein Barr Virus, oncogenes, or retroviruses, or other methods well known in the art.

In a preferred embodiment, the antibody is a chimeric or humanized antibody. Chimeric or humanized antibodies of the present invention can be prepared based on the sequence of a murine monoclonal antibody. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In another preferred embodiment, the antibody is a human antibody. Such human antibodies can be generated by immunizing transgenic or transchromosomic mice in which the endogenous mouse immunoglobulin genes have been inactivated and exogenous human immunoglobulin genes have been introduced. Such mice are known in the art (see e.g., U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. Nos. 5,939,598; 6,075,181; 6,114,598; 6,150,584 and 6,162,963 to Kucherlapati et al.; and PCT Publication WO 02/43478 to Ishida et al.) Human antibodies can also be prepared using phage display methods for screening libraries of human immunoglobulin genes. Such phage display methods for isolating human antibodies also are know in the art (see e.g., U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.).

Reactive Functional Groups

For clarity of illustration the following discussion focuses on the conjugation of a cytotoxin of the invention to a cleavable substrate. The focus exemplifies one embodiment of the invention from which, others are readily inferred by one of skill in the art. No limitation of the invention is implied, by focusing the discussion on a single embodiment.

Exemplary compounds of the invention bear a reactive functional group, which is generally located on a substituted or unsubstituted alkyl or heteroalkyl chain, allowing their facile attachment to another species. A convenient location for the reactive group is the terminal position of the chain.

Reactive groups and classes of reactions useful in practicing the present invention are generally those that are well known in the art of bioconjugate chemistry. The reactive functional group may be protected or unprotected, and the protected nature of the group may be changed by methods known in the art of organic synthesis. Currently favored classes of reactions available with reactive cytotoxin analogues are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Exemplary reaction types include the reaction of carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters. Hydroxyl groups can be converted to esters, ethers, aldehydes, etc. Haloalkyl groups are converted to new species by reaction with, for example, an amine, a carboxylate anion, thiol anion, carbanion, or an alkoxide ion. Dienophile (e.g., maleimide) groups participate in Diels-Alder. Aldehyde or ketone groups can be converted to imines, hydrazones, semicarbazones or oximes, or via such mechanisms as Grignard addition or alkyllithium addition. Sulfonyl halides react readily with amines, for example, to form sulfonamides. Amine or sulfhydryl groups are, for example, acylated, alkylated or oxidized. Alkenes, can be converted to an array of new species using cycloadditions, acylation, Michael addition, etc. Epoxides react readily with amines and hydroxyl compounds.

One skilled in the art will readily appreciate that many of these linkages may be produced in a variety of ways and using a variety of conditions. For the preparation of esters, see, e.g., March supra at 1157; for thioesters, see, March, supra at 362-363, 491, 720-722, 829, 941, and 1172; for carbonates, see, March, supra at 346-347; for carbamates, see, March, supra at 1156-57; for amides, see, March supra at 1152; for ureas and thioureas, see, March supra at 1174; for acetals and ketals, see, Greene et al. supra 178-210 and March supra at 1146; for acyloxyalkyl derivatives, see, PRODRUGS: TOPICAL AND OCULAR DRUG DELIVERY, K. B. Sloan, ed., Marcel Dekker, Inc., New York, 1992; for enol esters, see, March supra at 1160; for N-sulfonylimidates, see, Bundgaard et al., *J. Med. Chem.*, 31:2066 (1988); for anhydrides, see, March supra at 355-56, 636-37, 990-91, and 1154; for N-acylamides, see, March supra at 379; for N-Mannich bases, see, March supra at 800-02, and 828; for hydroxymethyl ketone esters, see, Petracek et al. *Annals NY Acad. Sci.*, 507:353-54 (1987); for disulfides, see, March supra at 1160; and for phosphonate esters and phosphonamidates.

The reactive functional groups can be unprotected and chosen such that they do not participate in, or interfere with, the reactions. Alternatively, a reactive functional group can be protected from participating in the reaction by the presence of a protecting group. Those of skill in the art will understand how to protect a particular functional group from interfering with a chosen set of reaction conditions. For examples of useful protecting groups, See Greene et al., PROTECTIVE GROUPS IN ORGANIC SYNTHESIS, John Wiley & Sons, New York, 1991.

Typically, the cleavable substrate is linked covalently to a cytotoxin using standard chemical techniques through their respective chemical functionalities.

Generally, prior to forming the linkage between the cytotoxin and the cleavable substrate at least one of the chemical functionalities will be activated. One skilled in the art will appreciate that a variety of chemical functionalities, including hydroxy, amino, and carboxy groups, can be activated using a variety of standard methods and conditions. In an exemplary embodiment, the invention comprises a carboxyl functionality as a reactive functional group. Carboxyl groups may be activated as described hereinabove.

Linkers

One or more self-immolative linker groups $L^1$ are optionally introduced between the cytotoxin and the cleavable substrate. These linker groups may also be described as spacer groups and contain at least two reactive functional groups. Typically, one chemical functionality of the spacer group bonds to a chemical functionality of the therapeutic agent, e.g., cytotoxin, while the other chemical functionality of the spacer group is used to bond to a chemical functionality of the cleavable substrate. Examples of chemical functionalities of spacer groups include hydroxy, mercapto, carbonyl, carboxy, amino, ketone, and mercapto groups.

The self-immolative linkers, represented by $L^1$, are generally substituted or unsubstituted alkyl, substituted or unsubstituted aryl, substituted or unsubstituted heteroaryl or substituted or unsubstituted heteroalkyl. In one embodiment, the alkyl or aryl groups may comprise between 1 and 20 carbon atoms. They may also comprise a polyethylene glycol moiety.

Exemplary spacer groups include, for example, 6-aminohexanol, 6-mercaptohexanol, 10-hydroxydecanoic acid, glycine and other amino acids, 1,6-hexanediol, β-alanine, 2-aminoethanol, cysteamine(2-aminoethanethiol), 5-aminopentanoic acid, 6-aminohexanoic acid, 3-maleimidobenzoic acid, phthalide, α-substituted phthalides, the carbonyl group, aminal esters, nucleic acids, peptides and the like.

The spacer can serve to introduce additional molecular mass and chemical functionality into the cytotoxin-cleavable substrate complex. Generally, the additional mass and functionality will affect the serum half-life and other properties of the complex. Thus, through careful selection of spacer groups, cytotoxin complexes with a range of serum half-lives can be produced. Preferably, upon cleavage of the cleavable substrate, the self-immolative spacer will spontaneously cleave from the drug.

Examples of Conjugates

Examples of suitable drug-cleavable substrate conjugates are illustrated below.

In each case, the drug is a CBI derivative. The first compound includes a drug coupled via two self-immolative spacers to a cleavable peptide which can be cleaved by an enzyme, preferably a tumor-associated enzyme, such as thimet oligopeptidase (TOP), CD10 (neprilysin), a matrix metallopretease (such as MMP2 or MMP9), a type II transmembrane serine protease (such as Hepsin, testisin, TMPRSS4, or matritriptase/MT-SP1), or a cathepsin. The second compound includes a drug coupled via a self-immolative spacer to a cephalosporin derivative that can be cleaved by an enzyme such as β-lactamase (e.g., by β-lactamase conjugated to a tumor-specific antibody).

Pharmaceutical Formulations and Administration

In another preferred embodiment, the present invention provides a pharmaceutical formulation comprising a compound of the invention and a pharmaceutically acceptable carrier.

The compounds described herein including pharmaceutically acceptable carriers such as addition salts or hydrates thereof, can be delivered to a patient using a wide variety of

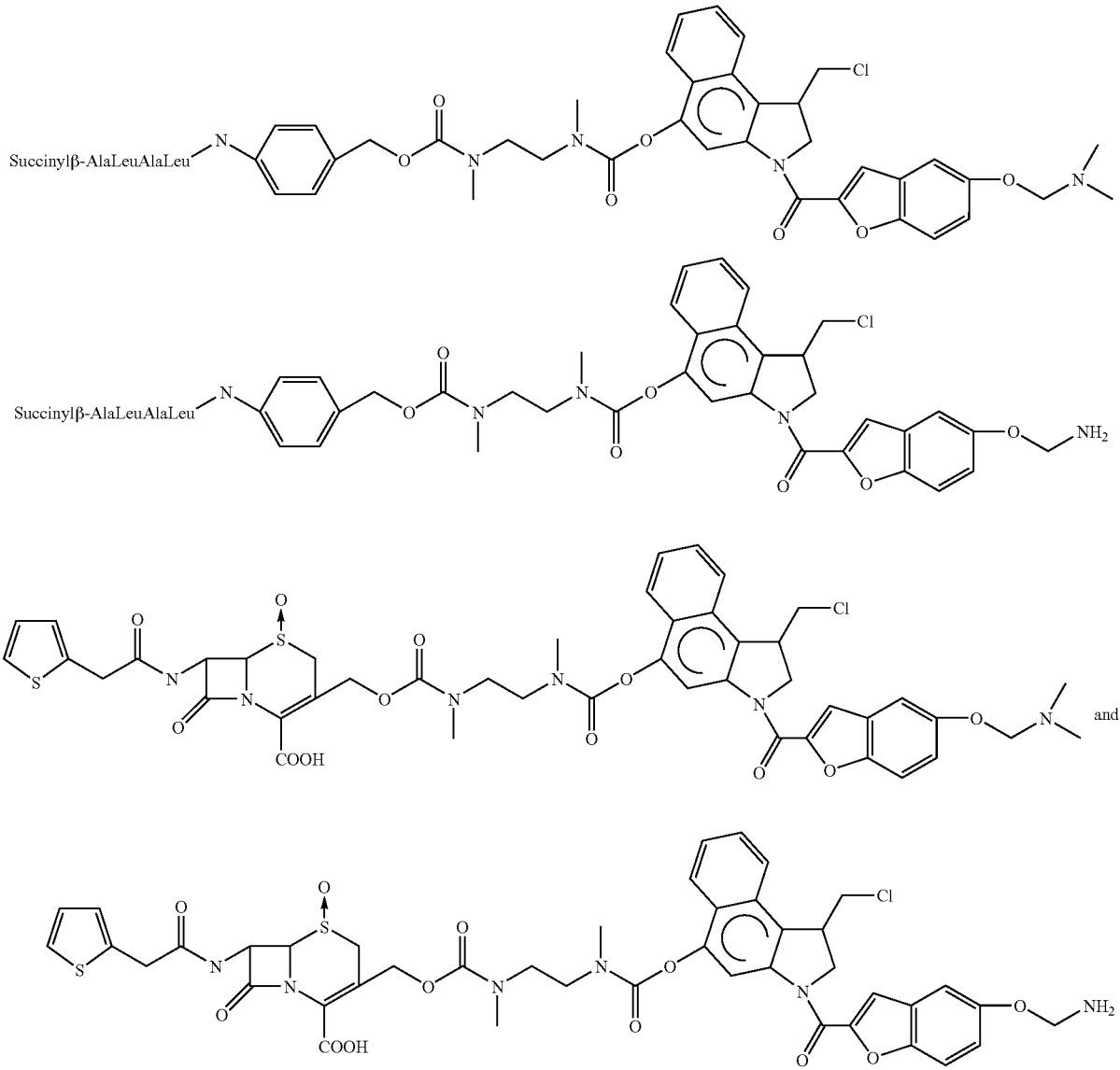

routes or modes of administration. Suitable routes of administration include, but are not limited to, inhalation, transdermal, oral, rectal, transmucosal, intestinal and parenteral administration, including intramuscular, subcutaneous and intravenous injections. Preferably, the conjugates of the invention are administered parenterally, more preferably intravenously.

As used herein, the terms "administering" or "administration" are intended to encompass all means for directly and indirectly delivering a compound to its intended site of action.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to patients suffering from a disease state caused by an organism that relies on an autoinducer, the compounds of the invention can be administered in cocktails containing agents used to treat the pain, infection and other symptoms and side effects commonly associated with the disease. Such agents include, e.g., analgesics, antibiotics, etc.

When administered to a patient undergoing cancer treatment, the compounds may be administered in cocktails containing anti-cancer agents and/or supplementary potentiating agents. The compounds may also be administered in cocktails containing agents that treat the side-effects of radiation therapy, such as anti-emetics, radiation protectants, etc.

Supplementary potentiating agents that can be co-administered with the compounds of the invention include, e.g., tricyclic anti-depressant drugs (e.g., imipramine, desipramine, amitriptyline, clomipramine, trimipramine, doxepin, nortriptyline, protriptyline, amoxapine and maprotiline); non-tricyclic and anti-depressant drugs (e.g., sertraline, trazodone and citalopram); $Ca^{+2}$ antagonists (e.g., verapamil, nifedipine, nitrendipine and caroverine); amphotericin; triparanol analogues (e.g., tamoxifen); antiarrhythmic drugs (e.g., quinidine); antihypertensive drugs (e.g., reserpine); thiol depleters (e.g., buthionine and sulfoximine); and calcium leucovorin.

The active compound(s) of the invention are administered per se or in the form of a pharmaceutical composition wherein the active compound(s) is in admixture with one or more pharmaceutically acceptable carriers, excipients or diluents. Pharmaceutical compositions for use in accordance with the present invention are typically formulated in a conventional manner using one or more physiologically acceptable carriers comprising excipients and auxiliaries, which facilitate processing of the active compounds into preparations which, can be used pharmaceutically. Proper formulation is dependent upon the route of administration chosen.

For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired. to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Injection is a preferred method of administration for the compositions of the current invention. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions. For injection, the agents of the invention may be formulated in aqueous solutions, preferably in physiologically compatible buffers such as Hanks's solution, Ringer's solution, or physiological saline buffer.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

A preferred pharmaceutical composition is a composition formulated for injection such as intravenous injection and includes about 0.01% to about 100% by weight of the drug conjugate, based upon 100% weight of total pharmaceutical composition. The drug conjugate may be an antibody-cytotoxin conjugate where the antibody has been selected to target a particular cancer.

Libraries

Also within the scope of the present invention are libraries of the cytotoxins and cytotoxin-cleavable substrates of the invention. Exemplary libraries include at least 10 compounds, more preferably at least 100 compound, even more preferably at least 1000 compounds and still more preferably at least 100,000 compounds. The libraries are in a form that is readily queried for a particular property, e.g., cytotoxicity, cleavage of a substrate by an enzyme, or other cleavage reagent. Exemplary forms include chip formats, microarrays, and the like.

Parallel, or combinatorial, synthesis has as its primary objective the generation of a library of diverse molecules which all share a common feature, referred to throughout this description as a scaffold. By substituting different moieties at each of the variable parts of the scaffold molecule, the amount of space explorable in a library grows. Theories and modern medicinal chemistry advocate the concept of occupied space as a key factor in determining the efficacy of a given compound against a given biological target. By creating a diverse library of molecules, which explores a large percentage of the targeted space, the odds of developing a highly efficacious lead compound increase dramatically.

Parallel synthesis is generally conducted on a solid phase support, such as a polymeric resin. The scaffold, or other suitable intermediate is cleavably tethered to the resin by a chemical linker. Reactions are carried out to modify the scaffold while tethered to the particle. Variations in reagents and/or reaction conditions produce the structural diversity, which is the hallmark of each library.

Parallel synthesis of "small" molecules (non-oligomers with a molecular weight of 200-1000) was rarely attempted prior to 1990. See, for example, Camps. et al., *Annaks de Quimica*, 70: 848 (1990). Recently, Ellmann disclosed the solid phase-supported parallel (also referred to as "combinatorial") synthesis of eleven benzodiazepine analogs along with some prostaglandins and beta-turn mimetics. These disclosures are exemplified in U.S. Pat. No. 5,288,514. Another relevant disclosure of parallel synthesis of small molecules may be found in U.S. Pat. No. 5,324,483. This patent discloses the parallel synthesis of between 4 and 40 compounds in each of sixteen different scaffolds. Chen et al. have also applied organic synthetic strategies to develop non-peptide libraries synthesized using multi-step processes on a polymer support. (Chen et al., *J. Am. Chem. Soc.*, 116: 2661-2662 (1994)).

Once a library of unique compounds is prepared, the preparation of a library of immunoconjugates, or antibodies can be prepared using the library of autoinducers as a starting point and using the methods described herein.

Kits

In another aspect, the present invention provides kits containing one or more of the compounds or compositions of the invention and directions for using the compound or composition. In an exemplary embodiment, the invention provides a kit for conjugating a linker arm of the invention to another molecule. The kit includes the linker, and directions for attaching the linker to a particular functional group. The kit may also include one or more of a cytotoxic drug, a cleavable substrate, pharmaceutical salts or buffers. The kit may also include a container and optionally one or more vial, test tube, flask, bottle, or syringe. Other formats for kits will be apparent to those of skill in the art and are within the scope of the present invention.

Purification

In another exemplary embodiment, the present invention provides a method for isolating a molecular target for a cleavable substrate-cytotoxin of the invention, which binds to the cleavable substrate $X^2$. The method preferably comprises, contacting a cellular preparation that includes the target with an immobilized compound, thereby forming a complex between the receptor and the immobilized compound.

The cytotoxin of the invention can be immobilized on an affinity support by any art-recognized means. Alternatively, the cytotoxin can be immobilized using one or more of the cleavable substrates of the invention.

In yet another exemplary embodiment, the invention provides an affinity purification matrix that includes a cleavable substrate of the invention.

The method of the invention for isolating a target will typically utilize one or more affinity chromatography techniques. Affinity chromatography enables the efficient isolation of species such as biological molecules or biopolymers by utilizing their recognition sites for certain supported chemical structures with a high degree of selectivity. The literature is replete with articles, monographs, and books on the subject of affinity chromatography, including such topics as affinity chromatography supports, crosslinking members, ligands and their preparation and use. A sampling of those references includes: Ostrove, *Methods Enzymol.* 182: 357-71 (1990); Ferment, *Bioeng.* 70: 199-209 (1990). Huang et al., *J. Chromatogr.* 492: 431-69 (1989); "Purification of enzymes by heparin-Sepharose affinity chromatography," *J. Chromatogr.*, 184: 335-45 (1980); Farooqi, *Enzyme Eng.*, 4: 441-2 (1978); Nishikawa, *Chem. Technol.*, 5(9): 564-71 (1975); Guilford et al., in, PRACT. HIGH PERFORM. LIQ. CHROMATOGR., Simpson (ed.), 193-206 (1976); Nishikawa, *Proc. Int. Workshop Technol. Protein Sep. Improv. Blood Plasma Fractionation*, Sandberg (ed.), 422-35; (1977) "Affinity chromatography of enzymes," *Affinity Chromatogr., Proc. Int. Symp.* 25-38, (1977) (Pub. 1978); and AFFINITY CHROMATOGRAPHY: A PRACTICAL APPROACH, Dean et al. (ed.), IRL Press Limited, Oxford, England (1985). Those of skill in the art have ample guidance in developing particular affinity chromatographic methods utilizing the materials of the invention.

In the present method, affinity chromatographic media of varying chemical structures can be used as supports. For example, agarose gels and cross-linked agarose gels are useful as support materials, because their hydrophilicity makes them relatively free of nonspecific binding. Other useful supports include, for example, controlled-pore glass (CPG) beads, cellulose particles, polyacrylamide gel beads and Sephadex™ gel beads made from dextran and epichlorohydrin.

Drug-Cleavable Substrate Conjugate Methods of Use

In addition to the compositions and constructs described above, the present invention also provides a number of methods that can be practiced utilizing the compounds and conjugates of the invention. Methods for using the drug-cleavable substrate conjugate of the current invention include: killing or inhibiting the growth or replication of a tumor cell or cancer cell, treating cancer, treating a pre-cancerous condition, killing or inhibiting the growth or replication of a cell that expresses an auto-immune antibody, treating an autoimmune disease, treating an infectious disease, preventing the multiplication of a tumor cell or cancer cell, preventing cancer, preventing the multiplication of a cell that expresses an auto-immune antibody, preventing an autoimmune disease, and preventing an infectious disease. These methods of use comprise administering to an animal such as a mammal or a human in need thereof an effective amount of a drug-cleavable substrate conjugate. In some embodiments, an enzyme is separately administered so that it becomes associated with the tumor or target cell.

The drug-cleavable substrate complex of the current invention is useful for treating, for example, cancer, autoimmune disease or infectious disease in an animal. Compositions and methods for treating tumors by providing a subject the composition in a pharmaceutically acceptable manner, with a pharmaceutically effective amount of a composition of the present invention are provided.

The current invention is particularly useful for the treatment of cancer and for the inhibition of the multiplication of a tumor cell or cancer cell in an animal. Cancer, or a precancerous condition, includes, but is not limited to, a tumor, metastasis, or any disease or disorder characterized by uncontrolled cell growth, can be treated or prevented by administration the drug-cleavable substrate complex of the current invention. The complex delivers the drug to a tumor cell or cancer cell. In one embodiment, the cleavable substrate is cleaved by an enzyme (or other entity that can cleave the substrate) that is associated with the tumor or other target cell. Once in contact with the enzyme, the cleavable substrate is cleaved by the enzyme, thereby releasing the drug. The released drug is then free to diffuse and induce cytotoxic activities. The cleavable substrate can be cleaved inside or outside of the tumor or target cell. The type of tumors or cancers that can be effectively treated can be altered by the choice of cleavable substrate and associated enzyme.

Representative examples of precancerous conditions that may be targeted by the drug-cleavable substrate conjugate, include, but are not limited to: metaplasia, hyperplasia, dysplasia, colorectal polyps, actinic ketatosis, actinic cheilitis, human papillomaviruses, leukoplakia, lychen planus and Bowen's disease.

Representative examples of cancers or tumors that may be targeted by the drug-cleavable substrate conjugate include, but are not limited to: lung cancer, colon cancer, prostate cancer, lymphoma, melanoma, breast cancer, ovarian cancer, testicular cancer, CNS cancer, renal cancer, kidney cancer, pancreatic cancer, stomach cancer, oral cancer, nasal cancer, cervical cancer and leukemias. It will be readily apparent to the ordinarily skilled artisan that the particular cleavable substrate used in the conjugate can be chosen such that it targets the drug to the tumor tissue to be treated with the drug.

In an embodiment, the present invention provides a method of killing a cell. The method includes administering to the cell an amount of a compound of the invention sufficient to kill said cell. In an exemplary embodiment, the compound is administered to a subject bearing the cell. In a further exemplary embodiment, the administration serves to retard or stop the growth of a tumor that includes the cell (e.g., the cell can be a tumor cell). For the administration to retard the growth, the rate of growth of the cell should be at least 10% less than the rate of growth before administration. Preferably, the rate of growth will be retarded at least 20%, 30%, 40%, 50%, 60%, 70%, 80%, 90%, or completely stopped.

Effective Dosages

Pharmaceutical compositions suitable for use with the present invention include compositions wherein the active ingredient is contained in a therapeutically effective amount, i.e., in an amount effective to achieve its intended purpose. The actual amount effective for a particular application will depend, inter alia, on the condition being treated. Determination of an effective amount is well within the capabilities of those skilled in the art, especially in light of the detailed disclosure herein.

For any compound described herein, the therapeutically effective amount can be initially determined from cell culture assays. Target plasma concentrations will be those concentrations of active compound(s) that are capable of inhibition cell growth or division. In preferred embodiments, the cellular activity is at least 25% inhibited. Target plasma concentrations of active compound(s) that are capable of inducing at least about 50%, 75%, or even 90% or higher inhibition of cellular activity are presently preferred. The percentage of inhibition of cellular activity in the patient can be monitored to assess the appropriateness of the plasma drug concentration achieved, and the dosage can be adjusted upwards or downwards to achieve the desired percentage of inhibition.

As is well known in the art, therapeutically effective amounts for use in humans can also be determined from animal models. For example, a dose for humans can be formulated to achieve a circulating concentration that has been found to be effective in animals. The dosage in humans can be adjusted by monitoring cellular inhibition and adjusting the dosage upwards or downwards, as described above.

A therapeutically effective dose can also be determined from human data for compounds which are known to exhibit similar pharmacological activities. The applied dose can be adjusted based on the relative bioavailability and potency of the administered compound as compared with the known compound.

Adjusting the dose to achieve maximal efficacy in humans based on the methods described above and other methods as are well-known in the art is well within the capabilities of the ordinarily skilled artisan.

In the case of local administration, the systemic circulating concentration of administered compound will not be of particular importance. In such instances, the compound is administered so as to achieve a concentration at the local area effective to achieve the intended result.

For use in the prophylaxis and/or treatment of diseases related to abnormal cellular proliferation, a circulating concentration of administered compound of about 0.001 µM to 20 µM is preferred, with about 0.01 µM to 5 µM being preferred.

Patient doses for oral administration of the compounds described herein, typically range from about 1 mg/day to about 10,000 mg/day, more typically from about 10 mg/day to about 1,000 mg/day, and most typically from about 50 mg/day to about 500 mg/day. Stated in terms of patient body weight, typical dosages range from about 0.01 to about 150 mg/kg/day, more typically from about 0.1 to about 15 mg/kg/day, and most typically from about 1 to about 10 mg/kg/day, for example 5 mg/kg/day or 3 mg/kg/day.

In at least some embodiments, patient doses that retard or inhibit tumor growth can be 1 µmol/kg/day or less. For example, the patient doses can be 0.9, 0.6, 0.5, 0.45, 0.3, 0.2, 0.15, or 0.1 µmol/kg/day or less (referring to moles of the drug) of the drug or a drug conjugate, such as an antibody-drug conjugate. Preferably, the drug or drug conjugate growth of the tumor when administered in the daily dosage amount over a period of at least five days. In at least some embodiments, the tumor is a human-type tumor in a SCID mouse. As an example, the SCID mouse can be a CB17.SCID mouse (available from Taconic, Germantown, N.Y.).

For other modes of administration, dosage amount and interval can be adjusted individually to provide plasma levels of the administered compound effective for the particular clinical indication being treated. For example, in one embodiment, a compound according to the invention can be administered in relatively high concentrations multiple times per day. Alternatively, it may be more desirable to administer a compound of the invention at minimal effective concentrations and to use a less frequent administration regimen. This will provide a therapeutic regimen that is commensurate with the severity of the individual's disease.

Utilizing the teachings provided herein, an effective therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds, compositions and methods of the present invention are further illustrated by the examples that follow. These examples are offered to illustrate, but not to limit the claimed invention.

EXAMPLES

Material and Methods

In the examples below, unless otherwise stated, temperatures are given in degrees Celsius (° C.); operations were carried out at room or ambient temperature (typically a range of from about 18-25° C.; evaporation of solvent was carried out using a rotary evaporator under reduced pressure (typically, 4.5-30 mmHg) with a bath temperature of up to 60° C.; the course of reactions was typically followed by TLC and reaction times are provided for illustration only; melting points are uncorrected; products exhibited satisfactory $^1$H-NMR and/or microanalytical data; yields are provided for illustration only; and the following conventional abbreviations are also used: mp (melting point), L (liter(s)), mL (milliliters), mmol (millimoles), g (grams), mg (milligrams), min (minutes), LC-MS (liquid chromatography-mass spectrometry) and h (hours).

$^1$H-NMR spectra were measured on a Varian Mercury 300 MHz spectrometer and were consistent with the assigned structures. Chemical shifts were reported in parts per million (ppm) downfield from tetramethylsilane. Electrospray mass spectra were recorded on a Perkin Elmer Sciex API 365 mass spectrometer. Elemental analyses were performed by Robertson Microlit Laboratories, Madison, N.J. Silica gel for flash chromatography was E. Merck grade (230-400 mesh). Reverse-Phase analytical HPLC was performed on either a HP 1100 or a Varian ProStar 210 instrument with a Phenomenex Luna 5 μm C-18(2) 150 mm×4.6 mm column or a Varian Microsorb-MV 0.1 μm C-18 150 mm×4.6 mm column. A flow rate of 1 mL/min was with either a gradient of 0% to 50% buffer B over 15 minutes or 10% to 100% buffer B over 10 minutes with detection by UV at 254 nm. Buffer A, 20 mM ammonium formate+20% acetonitrile or 0.1% trifluoroacetic acid in acetonitrile; buffer B, 20 mM ammonium formate+80% acetonitrile or 0.1% aqueous trifluoroacetic acid. Reverse phase preparative HPLC were performed on a Varian ProStar 215 instrument with a Waters Delta Pak 15 μm C-18 300 mm×7.8 mm column.

Example 1

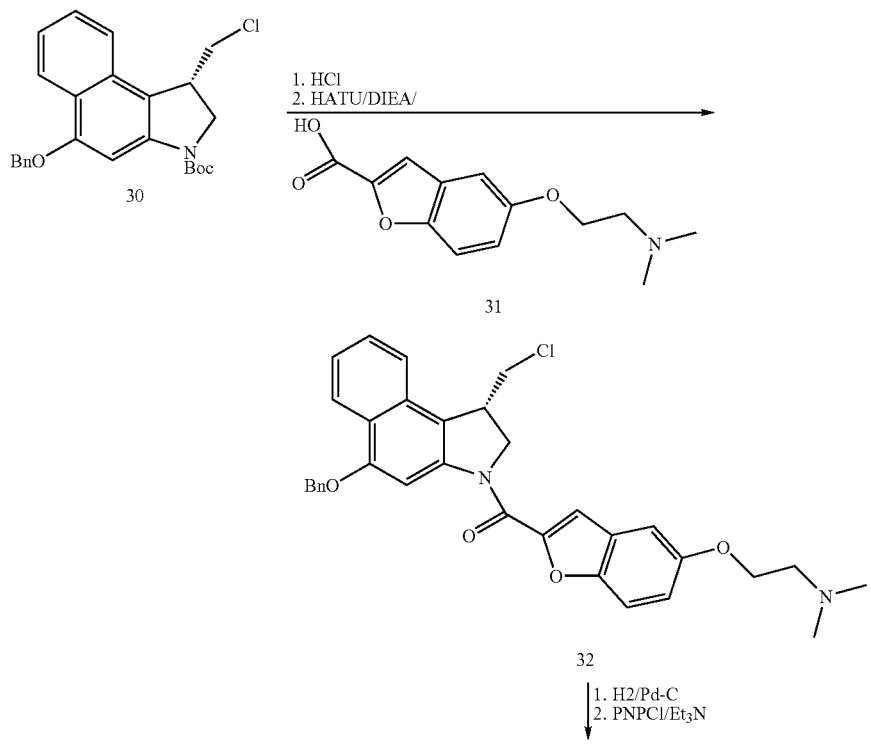

35

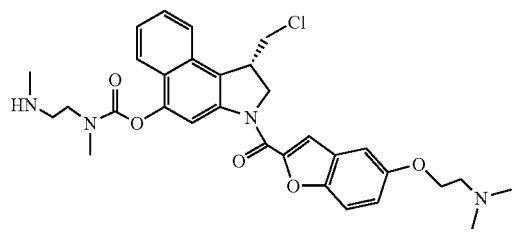

34

-continued

36

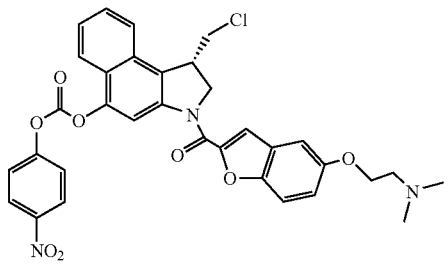

33

Synthesis of Compound 32. To a solution of Compound 30 (120 mg, 0.28 mmole) in ethyl acetate (10 mL) was bubbled HCl gas for 5 min. The reaction mixture was stirred at RT for another 30 min and then the mixture was concentrated. Ether was added to the reaction mixture and the white precipitate was collected on a filter funnel. Solid was dried overnight under vacuum to give 100 mg of the desired product which was confirmed by LC-MS (ESI) 324 (M+H$^+$) and used in next step without further purification. To a solution of this compound (100 mg, 0.24 mmole) in DMF (5 mL) were added compound 31 (65 mg, 0.26 mmole), HATU (100 mg, 0.26 mmole) and TEA (91 uL, 0.52 mmole). The mixture thus obtained was stirred at room temperature for 3 hrs. The solvent was evaporated and the residue was purified on semi-preparative HPLC with 0.1% TFA in water and acetonitrile as eluent to give compound 32 as an oil (110 mg, 80%). The desired product was confirmed by LC-MS (ESI) 555 (M+H$^+$).

Synthesis of Compound 33. A solution of Compound 32 (110 mg, 0.2 mmole) and palladium on charcoal (20 mg) in DCM (10 mL) and methanol (5 mL) was stirred under hydrogen atmospheric pressure at room temperature for 12 hrs. The palladium was filtrated and the reaction mixture was concentrated and the residue was purified on semi-preparative HPLC with 0.1% TFA in water and acetonitrile as eluent to give the desired compound as an oil (80 mg, 78%) LC-MS (ESI) 465 (M+H$^+$). To a solution of the residue (80 mg, 0.17 mmole) in dichloromethane (10 mL) and THF (5 mL) was added PNPCl (4-nitrophenyl chloroformate) (137 mg, 0.68 mmole) and triethyl amine (144 uL, 1.02 mmol) at 0° C. The mixture thus obtained was stirred for 30 min at 0° C. and then at room temperature for 12 hrs. The reaction mixture was concentrated under vacuum, and the residue was precipitated using ethyl ether (100 mL) to give compound 33 as a yellow solid (90 mg, 82%) which was dried under vacuum and confirmed by LC-MS (ESI) 631 (M+H$^+$).

Synthesis of Compound 34. To a solution of compound 33 (60 mg, 0.1 mmole) in dichloromethane (10 mL) was added Boc-N,N dimethyl entyl diamaine (84 mg, 0.38 mmole) and triethyl amine (26 uL, 0.1 mmol) at room temperature. The mixture thus obtained was stirred at room temperature for 12 hrs. The reaction mixture was concentrated under vacuum, and the residue was precipitated using ethyl ether (100 mL) to give Boc protected compound 34 which was used for the next step without further purification. Boc protected compound 34 was dissolved in 10 mL of TFA and the reaction mixtured was stirred at room temperature for 60 min. The reaction mixture was concentrated under vacuum, and the residue was precipitated using ethyl ether (100 mL) to give compound 34 as a yellow solid which was dried under vacuum and confirmed by LC-MS (ESI) 631 (M+H$^+$).

Example 2

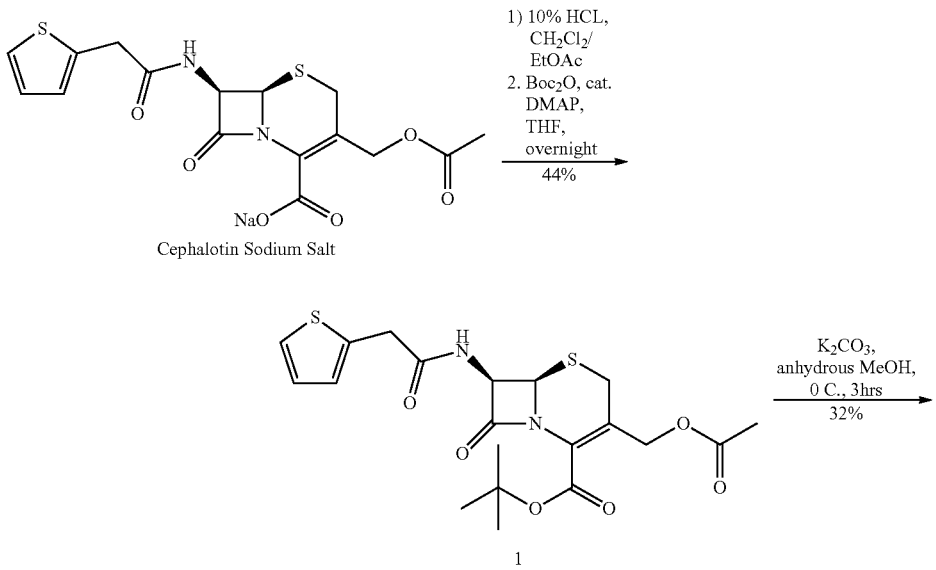

-continued
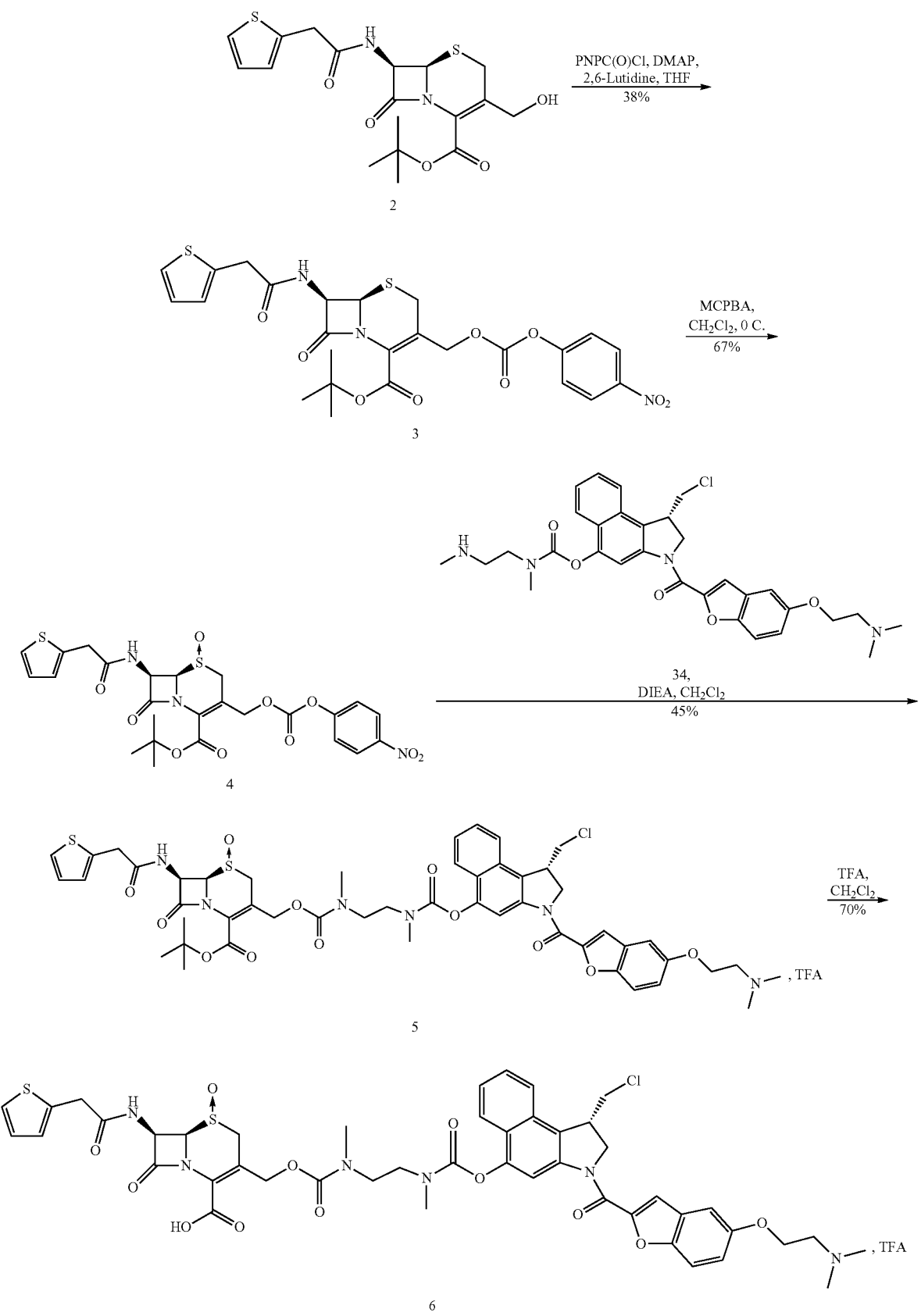

Synthesis of Compound 1 Cephalotin Sodium salt (0.5 g, 1.2 mmole) was dissolved in water (10 mL) and poured into a separative funnel. The solution was acidified with 1N HCl aqueous solution and the desired compound was extracted with Dichloromethane (100 mL) and Ethyl Acetate (40 mL). The organic layer was dried over $Na_2SO_4$ anhydrous, filtered and concentrated to dryness to give the title compound as a white solid (474 mg, 99%). To a solution of the white compound (1.2 mmole) and tert-$Boc_2O$ (0.3 g, 1.37 mmole) in Tetrahydrofuran (20 mL) was added Dimethylaminopyridine (15 mg, 0.12 mmole). The mixture thus obtained was stirred at room temperature overnight. The solvent was evaporated and the residue was purified on semi-preparative HPLC with 0.1% TFA in Water and Acetonitrile as eluent to give the title compound as an oil (238 mg, 44%). $^1$H NMR ($CD_3OD$) δ 1.49 (s, 9H), 2.05 (s, 3H), 3.80 (s, 2H), 4.60 (d, 1H), 4.77 (d, 1H), 4.93 (d, 1H), 5.28 (d, 1H), 5.49 (m, 1H), 6.59 (s, 1H), 6.96 (m, 2H), 7.27 (dd, 1H), 9.18 (bd, 1H); LC-MS (ESI) 453 ($M+H^+$), 475 ($M+Na^+$), 491 ($M+K^+$).

Synthesis of Compound 2 To a solution of Compound 1 (204 mg, 0.45 mmole) in Methanol (40 mL) was added Potassium Carbonate (25 mg, 0.18 mmole) at 0° C. The mixture thus obtained was stirred for 3 hours. The reaction mixture was neutralized with Acetic Acid (600 μL) and concentrated. The solvent was evaporated and the residue was purified on semi-preparative HPLC with 0.1% TFA in Water and Acetonitrile as eluent to give the title compound as an oil (59 mg, 32%). $^1$H NMR ($CD_3OD$) δ 1.49 (s, 9H), 3.80 (s, 2H), 4.15 (m, 2H), 4.95 (d, 1H), 5.28 (d, 1H), 5.46 (m, 1H), 6.39 (d, 1H), 6.95 (m, 2H), 7.26 (m, 1H), 9.09 (bd, 1H); LC-MS (ESI) 410 ($M+H^+$), 433 ($M+Na^+$), 449 ($M+K^+$).

Synthesis of Compound 3 To a solution of Compound 2 (15 mg, 0.036 mmole) in THF (0.2 mL) was added Dimethylaminopyridine (0.13 mg, 0.001 mmole), para-Nitrophenyl chloroformate (11 mg, 0.054 mmole) and 2,6-Lutidine (6.4 μL, 0.054 mmole) at room temperature. The mixture thus obtained was stirred overnight. The solvent was evaporated and the residue was purified on semi-preparative HPLC with 0.1% TFA in Water and Acetonitrile as eluent to give the title compound as an oil (8 mg, 38%). $^1$H NMR ($CDCl_3$) δ 1.49 (s, 9H), 3.88 (s, 2H), 4.76 (d, 1H), 4.94 (d, 1H), 4.95 (s, 1H), 5.29 (m, 1H), 5.67 (m, 1H), 6.41 (d, 1H), 6.52 (s, 1H), 7.00 (m, 2H), 7.28 (m, 1H), 7.37 (dd, 2H), 8.29 (dd, 2H); LC-MS (ESI) 575 ($M+H^+$), 598 ($M+Na^+$), 614 ($M+K^+$).

Synthesis of Compound 4 To a solution of Compound 3 (18 mg, 0.031 mmole) in dichloromethane (0.5 mL) cooled to 0° C. was added m-Chloroperoxybenzoic acid (9 mg, 0.052 mmole). The mixture thus obtained was stirred for 2 hours at 0° C. The solvent was evaporated and the residue was purified on semi-preparative HPLC with 0.1% TFA in Water and Acetonitrile as eluent to give the title compound as an oil (12 mg, 67%). $^1$H NMR ($CDCl_3$) δ 1.54 (s, 9H), 3.31 (d, 1H), 3.87 (s, 2H), 3.88 (d, 1H), 4.53 (d, 1H), 4.88 (d, 1H), 4.59 (d, 1H), 6.10 (dd, 1H), 6.92 (d, 1H), 6.99 (m, 2H), 7.27 (d, 1H), 7.37 (dd, 2H), 8.28 (d, 2H); LC-MS (ESI) 591 ($M+H^+$), 614 ($M+Na^+$), 630 ($M+K^+$).

Synthesis of Compound 5 To a solution of Compound 34 (11 mg, 0.013 mmole) in 10% Dimethylformamide in Dichloromethane (0.2 mL) was added a solution of compound 4 (10 mg, 0.017 mmole) in Dichloromethane (0.2 mL), and Diisopropylethylamine (3.5 μL, 0.020 mmole) at room temperature. The mixture thus obtained was stirred overnight. The solvent was evaporated and the residue was purified on semi-preparative HPLC with 0.1% TFA in Water and Acetonitrile as eluent to give the title compound as an oil (7 mg, 45%). LC-MS (ESI) 1031 ($M+H^+$), 1054 ($M+Na^+$), 1070 ($M+K^+$).

Synthesis of Compound 6 To a solution of Compound 5 (6.5 mg, 0.0056 mmole) in Dichloromethane (0.2 mL) was added Trifluoroacetic Acid (0.1 mL) at 0° C. The mixture thus obtained was let warmed to room temperature and stirred for 30 min. The solvent was evaporated and the residue was purified on semi-preparative HPLC with 0.1% TFA in Water and Acetonitrile as eluent to give the title compound as an oil (4 mg, 70%). LC-MS (ESI) 975 ($M+H^+$), 998 ($M+Na^+$), 1014 ($M+K^+$).

Example 3

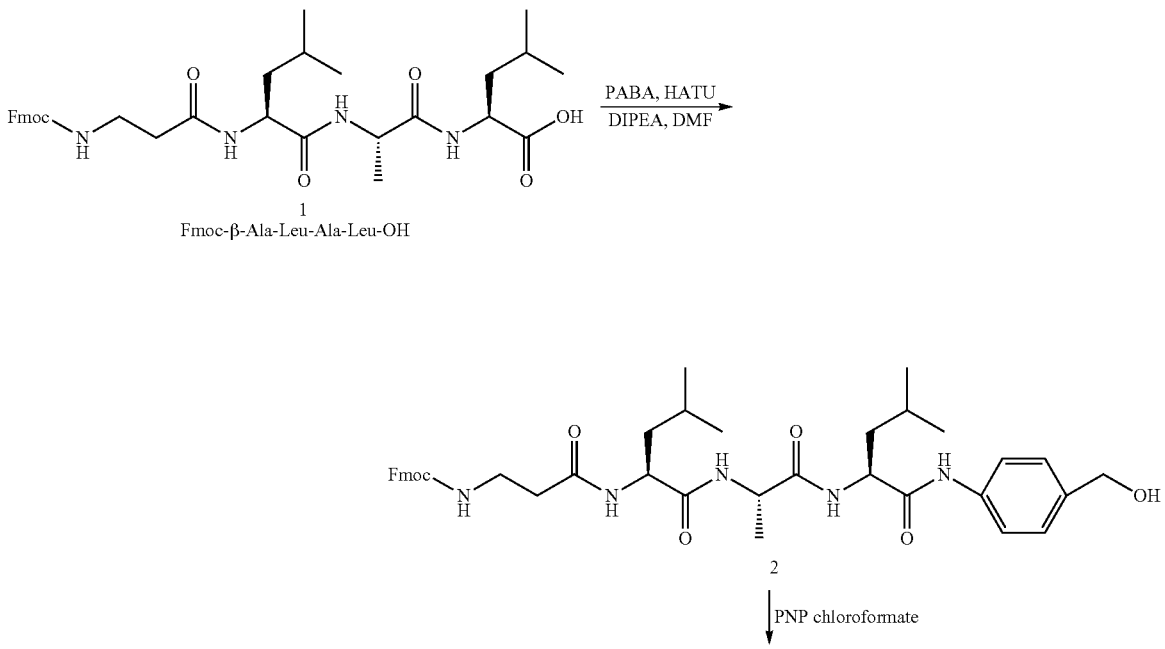

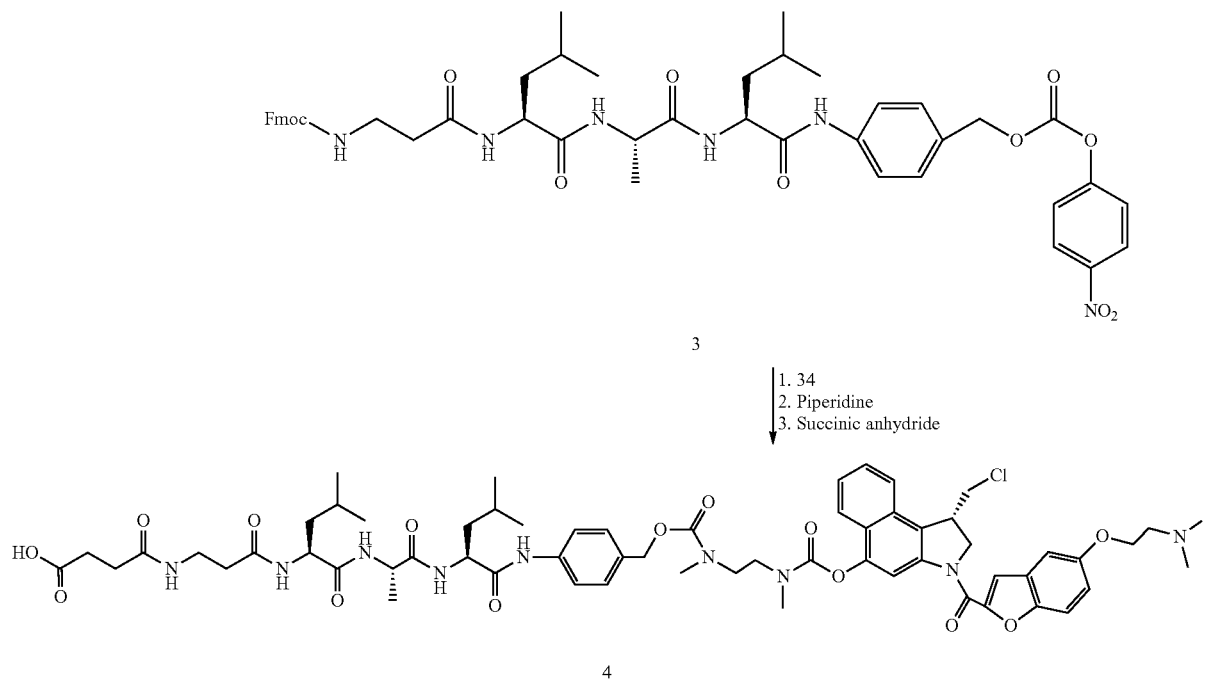

Synthesis of compound 2. In a 50 ml round bottom flask equipped with stir bar and nitrogen inlet, Fmoc-βAlaLeuAla-Leu-OH (5 gm, 0.0082 moles, Abbott Labs) was dissolved in DMF (30 ml). HATU (3.13 gm, 0.0082 moles) then DIPEA (2.86 ml, 0.0164 moles) were added and the solution stirred for 10 minutes. 4-Aminobenzyl alcohol (1.5 gm, 0.0122 moles) was added and the reaction stirred at room temperature for 18 hrs. The solvent was concentrated in vacuo and the residue dissolved in DMF (20 ml). The product was precipitated with diethyl ether (200 ml) and collected by filtration to give 4.5 gm (77%) of product. The product was confirmed by mass spec: m/z 714.4 [M+1]$^+$ Synthesis of compound 3. In a 25 ml RBF equipped with stir bar and nitrogen inlet, 2 (0.3 gm, 0.4 mmoles) was dissolved in 1.5 ml DMF. A 1:1 solution of DCM/THF was added followed by 4-nitrophenylchloroformate (0.2 gm, 1 mmole) and pyridine (0.2 ml, 2.5 mmoles). The reaction was stirred at room temperature for 6 hr. The solvent was removed in vacuo and the residue purified by column chromatography (10% MeOH/DCM) to yield 0.104 gm (28%) of 3. The product was confirmed by mass spec: m/z 879.6 [M+1]$^+$ Synthesis of Compound 4. To a solution of Compound 34 (11 mg, 0.013 mmole) in 10% Dimethylformamide in Dichloromethane (0.2 mL) was added a solution of compound 3 (15 mg, 0.017 mmole) in Dichloromethane (0.2 mL), and Diisopropylethylamine (3.5 µL, 0.020 mmole) at room temperature. The mixture thus obtained was stirred overnight. The solvent was evaporated and the residue was purified on semi-preparative HPLC with 0.1% TFA in Water and Acetonitrile as eluent to give the title compound as an oil. The product was confirmed by LC/MS. This product was dissolved in DMF (10 mL) and Piperidine (0.5 ml, 0.5 moles) was added and the solution stirred for 30 minutes. The solution was concentrated in vacuo, washed with hexane and dried under vacuum for 1.2 hrs. The deprotected amine prepared above was dissolved in anhydrous DMF (10 ml) followed by the addition of succinic anhydride (20 mg, 0.2 mmoles) and the reaction mixture was stirred at room temperature for 24 hr. After 24 hrs HPLC showed no starting material and the reaction was purified by preparative HPLC to yield compound 4. Compound 4 was confirmed by mass spec: m/z 1196 [M+1]$^+$ Example 4

Proliferation Assays

The biological activity of the cytotoxic compounds of the invention can be assayed using the well established $^3$H-thymidine proliferation assay. This is a convenient method for quantitating cellular proliferation, as it evaluates DNA synthesis by measuring the incorporation of exogenous radiolabeled $^3$H-thymidine. This assay is highly reproducible and can accommodate large numbers of compounds.

To carry out the assay, promyelocytic leukemia cells, HL-60, are cultured in RPMI media containing 10% heat inactivated fetal calf serum (FCS). On the day of the study, the cells are collected, washed and resuspended at a concentration of $0.5 \times 10^6$ cells/ml in RPMI containing 10% FCS. 100 µl of cell suspension is added to 96 well plates. Serial dilutions (3-fold increments) of doxorubicin (as a positive control) or test compounds are made and 100 µl of compounds are added per well. Finally 10 µl of a 100 µCi/ml $^3$H-thymidine is added per well and the plates are incubated for 24 hours. The plates are harvested using a 96 well Harvester (Packard Instruments) and counted on a Packard Top Count counter. Pour parameter logistic curves are fitted to the $^3$H-thymidine incorporation as a function of drug molarity using Prism software to determine IC$_{50}$ values.

The compounds of the invention generally have an IC$_{50}$ value in the above assay of from about 1 pM to about 100 nM, preferably from about 10 pM to about 10 nM.

Example 5

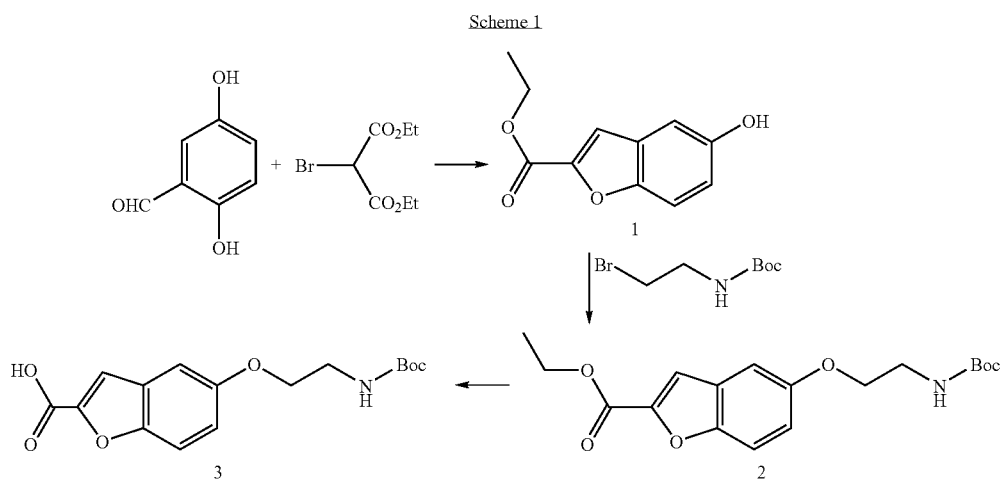

Synthesis of Compound 1

2,5-dihydroxybenzaldehyde (5.6 g, 40.57 mMoles) was dissolved in N-methylpyrrolidone 45 mL followed by addition of potassium carbonate (5.6 g, 40.5 mMoles). This was followed by addition of tetrabutyl ammonium bromide 260 mg (0.8 mMoles) and then of diethyl 2-bromomalonate (10.5 g, 7.5 mL, 44 mMoles). All the above additions were done at room temperature. The reaction mixture was stirred at 140° C. for 5 hours. TLC and HPLC revealed no starting material left and formation of a new peak. The reaction mixture was filtered through a silica pad and concentrated. 400 mL of 1N HCl was added to the crude and extracted with ethyl acetate. The organic phase was washed with brine and evaporated dry over anhydrous sodium sulfate. The crude product was purified by Silica Gel Flash Chromatography (hexanes/ethyl acetate, 5/1 respectively) to give 2 grams of compound 1 (23% yield). $H^1$NMR, Acetone-$d_6$: 1.37 (t, 3H), 4.37 (dd, 2H), 7.51 (s, 1H), 7.4 (d, 1H), 7.06 (s, 1H), 7.02 (d, 1H), 8.41 (s, 1H)

Synthesis of Compound 2

2-(boc-amino) ethyl bromide (344 mg, 1.53 mMoles) was added dropwise to stirring reaction mixture of compound 1 (100 mg, 0.48 mMoles) in DMF 5 mL, and potassium carbonate (132 mg, 0.955 mMoles) at 45° C. and the allowed to stir over the weekend. The solvent was evaporated. The crude was dissolved in ethyl acetate and washed with 0.2 N NaOH several times. The solvent was evaporated and the crude reaction mixture was purified by Silica Gel Flash Chromatography using ethyl acetate/hexanes (1:4, 2:4) giving 137 mg (81%) of compound 2. Mass Spec. $M^{[+1]}$=350.9. $H^1$ NMR, $CDCl_3$: 1.43 (s, 9H), 1.39 (t, 3H), 3.54 (m, 2H), 4.02 (t, 2H), 4.41 (dd, 2H), 7.01-7.03 (aromatic, 2H), 7.42-7.46 (aromatic, 2H)

Synthesis of Compound 3

Compound 2 was dissolved in MeOH and stirred for 2-3 hours in aqueous 2N NaOH solution. The solvent was evaporated, 10% citric acid solution was added, and the compound extracted with ethyl acetate. The product was further purified by reverse phase HPLC to give compound 3. Mass Spec, $M^{[+Na]}$ 344.5, $M^{[+K]}$ 360.5, $H^1$ NMR, Acetone-$d_6$: 1.41 (s, 9H), 3.49 (dd, 2H), 4.10 (t, 2H), 6.24 (broad, 1H), 7.13 (1H, aromatic), 7.29 (1H, aromatic), 7.54 (1H, aromatic), 7.58 (1H, aromatic).

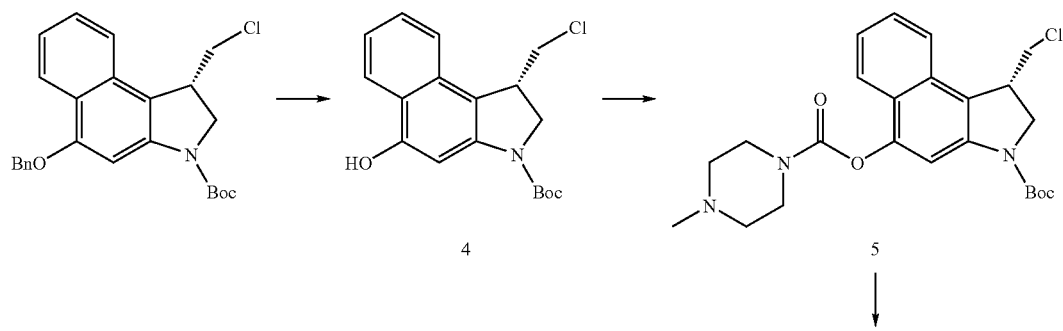

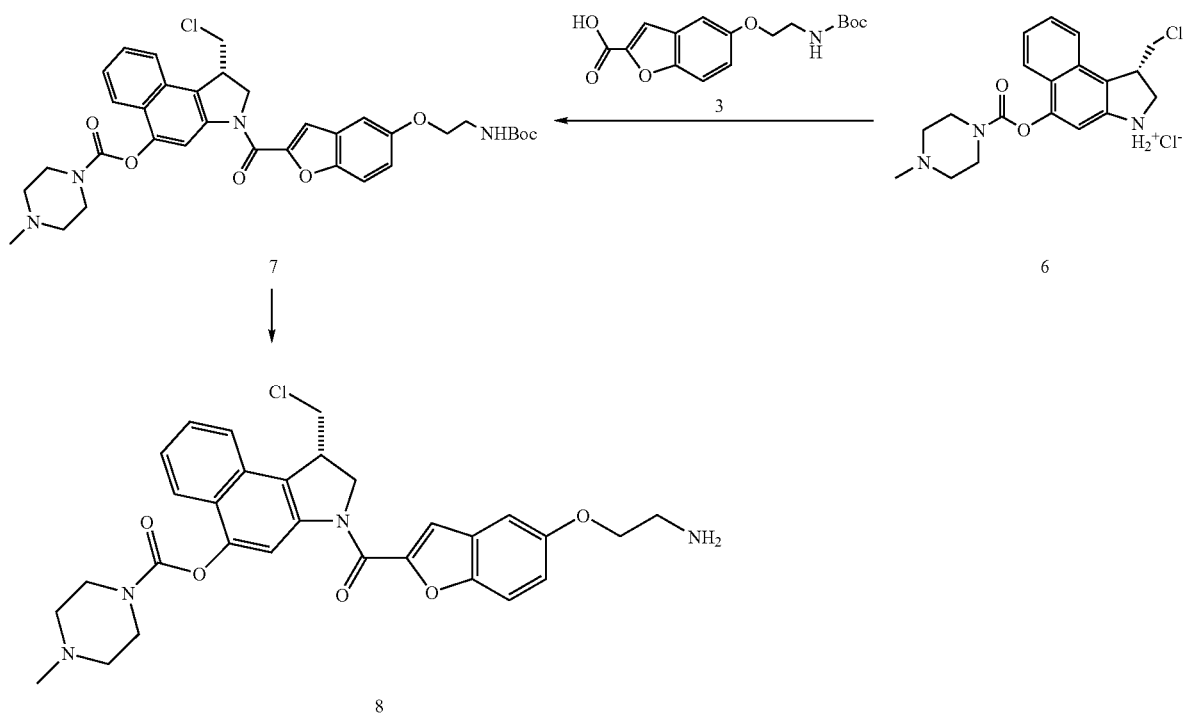

Boc, benzyl CBI (200 mg, 0.4728 mMoles) was debenzylated by hydrogenolysis using 10% Pd/C in DCM/MeOH 2:1 over a period of 8 hours. (Methods for making Boc, benzyl CBI or similar compounds are described in, for example, U.S. Provisional Patent Application Ser. No. 60/730,804; U.S. Pat. No. 6,534,660; and D. L. Boger et al., J. Org. Chem. 57, 2873-2876 (1992), all of which are incorporated by reference.) The catalyst was filtered and the crude greenish product was purified by Silica Gel chromatography with 5-20% ethyl acetate in hexanes give the desired compound 4 (150 mg 95% yield). Compound 4 (76 mg, 0.23 mMoles) was dissolved in DCM 8 mL and allyl alcohol 0.3 mL followed by the addition of 4-methyl piperazine carbonyl chloride, HCl salt (183 mg, 0.93 mMoles), pyridine (187 µL, 2.32 in Moles) and allowed to stir overnight. The crude product was purified by reverse phase chromatography on a C-18 column to give compound 5 (95 mg, 89% overall yield. Mass Spec: $M^{[+1]}$= 461, $M^{[+Na]}$=482, $M^{[+K]}$=498. Compound 5 was deprotected using a freshly prepared HCl-ethyl acetate solution to give compound 6.

Synthesis of Compound 8

5-(2-(tert-butoxycarbonyl)ethoxy)benzofuran-2-carboxylic acid (3, 24.4 mg, 0.076 mMoles) was dissolved in 1 mL DMF, TBTU (25 mg, 0.076 mMoles) was added followed by the addition of compound 6 (25 mg, 0.058 mMoles) and finally DIPEA (37 uL, 0.21 mMoles) and allowed to stir for 9 hours. The solvent was evaporated and the crude was purified by reverse phase HPLC to give 15 mgs of compound 7, 30% yield after lyophilization. Mass Spec: $M^{[+1]}$=663.4

Boc group from compound 7 was removed using freshly prepared solution of HCl in ethyl acetate to give compound 8 as its HCl salt.

Synthesis of Fmoc-Val-Cit-PABA

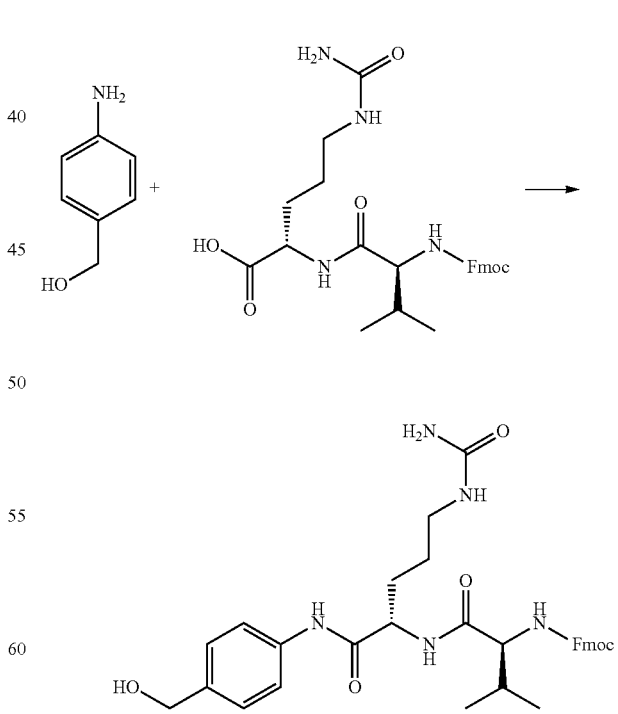

Fmoc-Val-Citruline (1.5 g, 3.02 mMoles) was dissolved in a mixture of DCM 14 µL and MeOH 7 mL. 4-amino benzylalcohol (445.2 mg, 3.62 mMoles) was added followed by 2-ethoxy-1-ethoxycarbonyl-1,2-dihydroquinoline (EEDQ) (1.5 g, 6.0 mMoles) and the reaction mixture was stirred for overnight. The solvent was removed and to the residue was added diethyl ether and sonicated for 5-10 minutes. The solid residue was allowed to settle down and the solvent decanted. This was repeated 2 more times to give 1.5 grams of Fmoc-Val-Cit-PABA (82% yield). $M^{[+1]}$=602.6, $M^{[+Na]}$=624.8, $M^{[+K]}$=640.6

Synthesis of Fmoc-Val-Cit-PABA-PNP

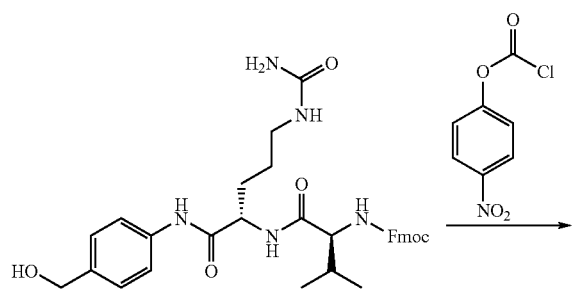

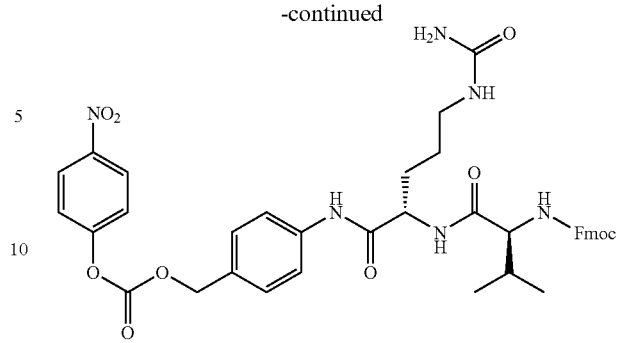

Fmoc-Val-Cit-PABA (65 mg, 0.11 mMoles) was dissolved in 2 mL DMF followed by addition of pyridine (36 uL, 0.44 mMoles). p-Nitrophenol chloroformate (66 mg, 0.33 mMoles) dissolved in THF (2 mL) was added dropwise. The reaction was completed in less then an hour. The solvent was evaporated and the crude purified by silica gel column using 5% MeOH in DCM to give 43 mg of desired product. 51% yield. Mass Spec: $M^{[+1]}$ 768.

Synthesis of Compound 11

Scheme 3

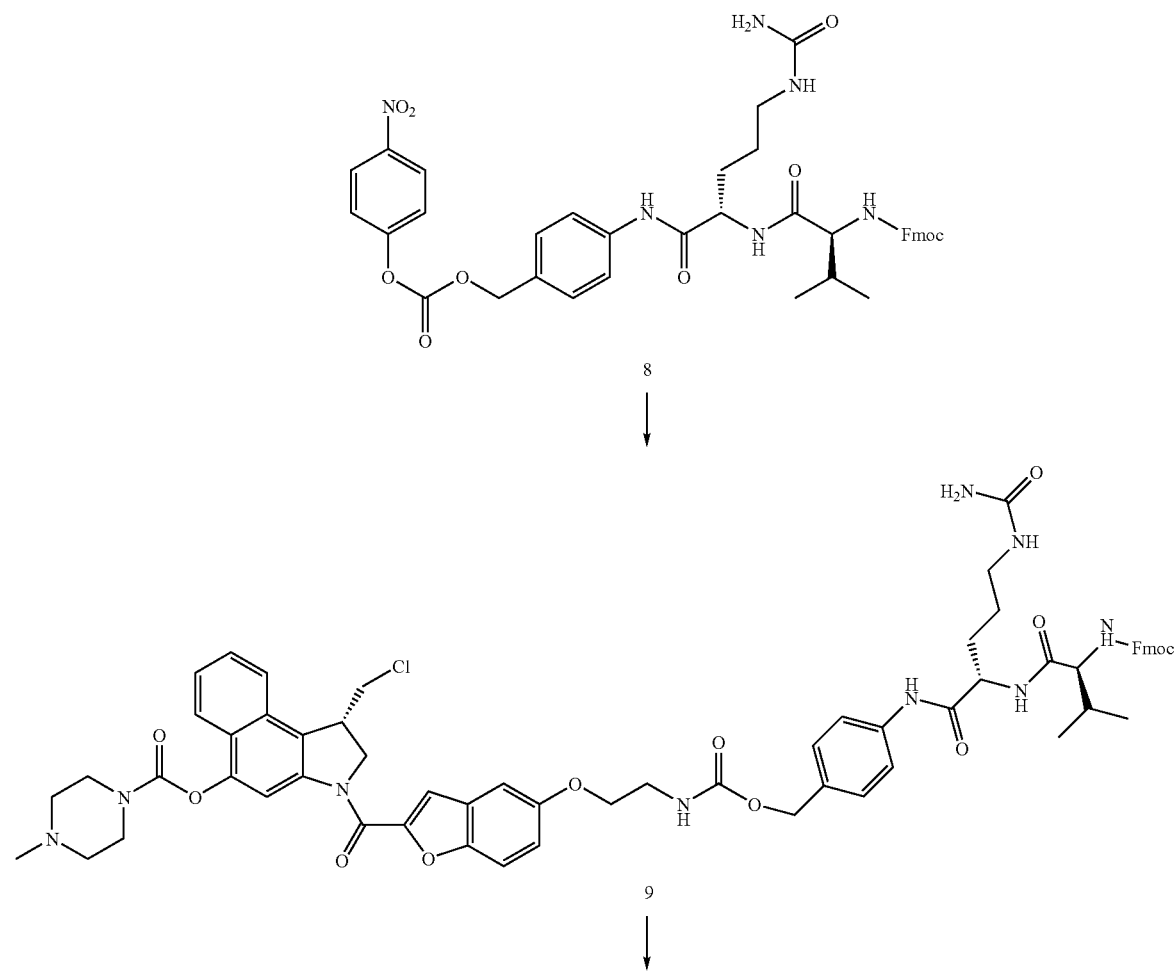

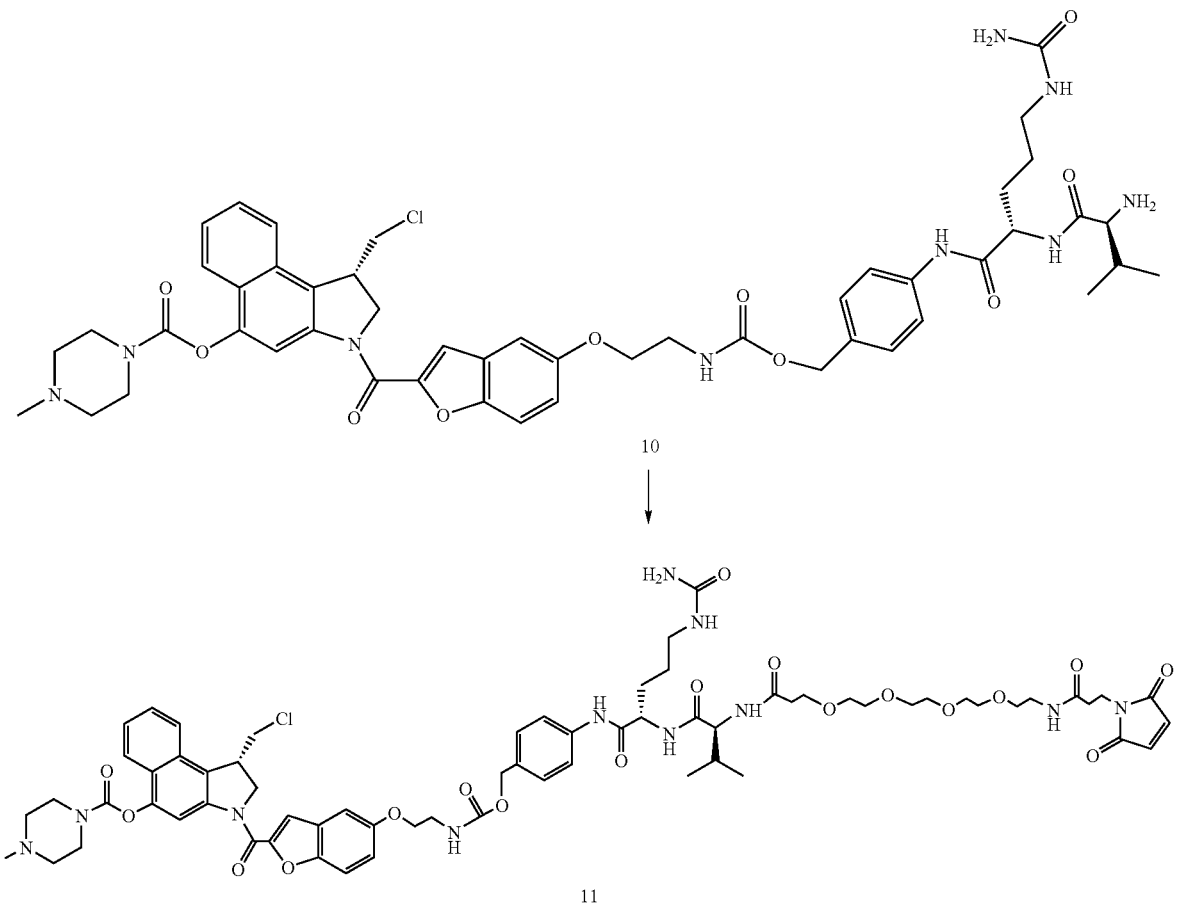

To a flask containing Fmoc-Val-Cit-PABA-PNP carbonate (13 mg, 0.017 mmoles) was added a solution of compound 8 (9.5 mg, 0.015 mMoles) in DMF 1 mL followed by the addition of DIPEA (15 μL). The reaction was over in less then 30 minutes. The solvent was evaporated and the crude purified by Reverse phase HPLC to give 9.0 mg of compound 9. Mass Spec: M[+1]=1191, M[+Na]=1213, M[+K]=1229

Fmoc protecting group of compound 9 (9 mg, 0.0076 mMoles) was removed using 5% piperidine in DMF 3 mL. The solvent was evaporated and the crude residue was rinsed with hexanes and diethyl ether. Compound 10 was dried overnight under high vacuum and used in the next step without any further treatment/purification. Mass Spec M[+1]=969, M[+Na]=991, M[+K]=1007. Compound 10 was reacted with Maleimide-TEG-NHS ester in DMF the reaction mixture was allowed to stir for 1 hour the solvent was evaporated and purified by Reverse Phase HPLC on a C-18 column to give 5 mg (48% yield) of compound 11. M[+1]=1367

Synthesis of Compound 12

Scheme 4

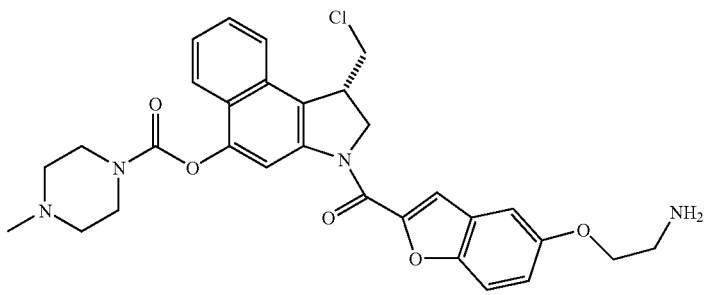

-continued
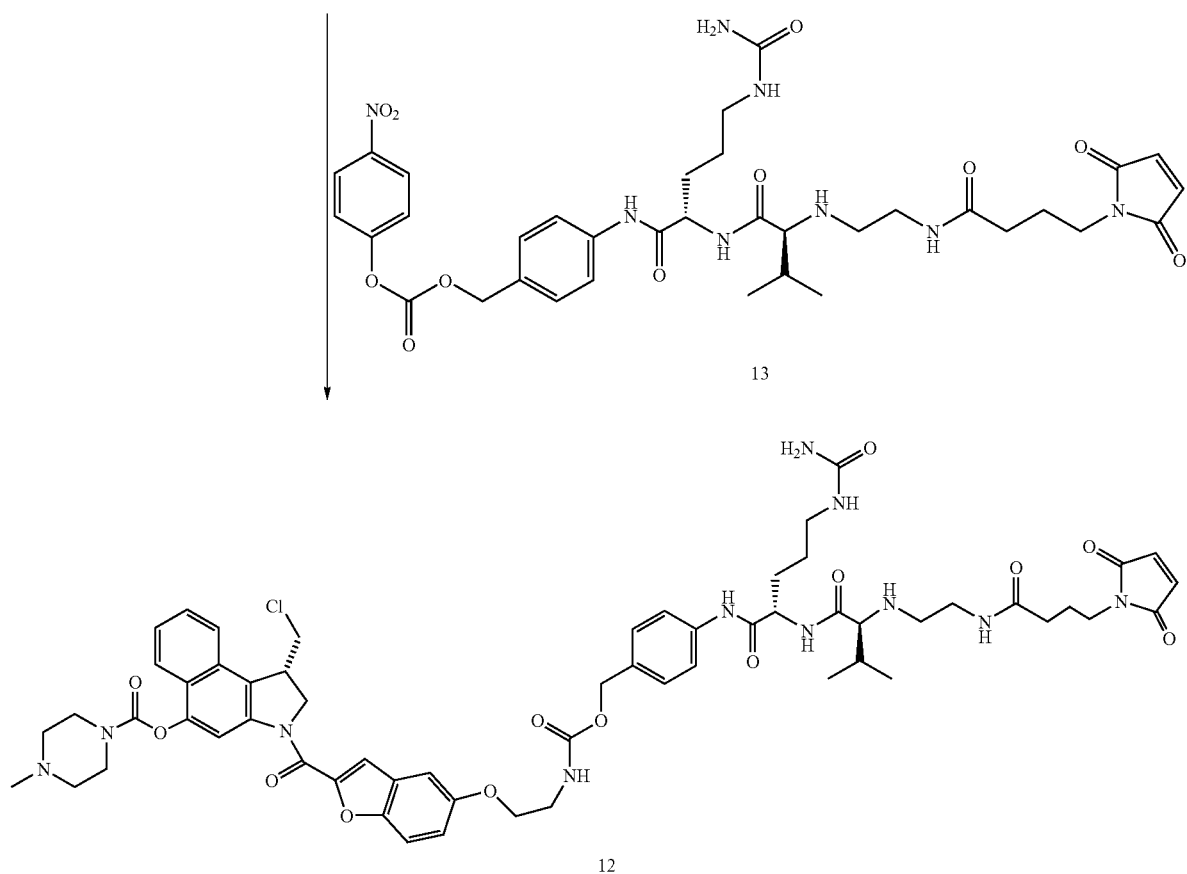
Compound 8 (8.5 mg, 0.013 mMoles) and Compound 13 (10 mg, 0.013 mMoles) were dissolved in DMF 1.5 mL followed by addition of DIPEA (7 μL, 0.039 mMoles) the reaction was completed in 50 minutes, the solvent was evaporated and purified by reverse Phase HPLC on a Gemini C-18 column (Phenomenex Inc., Torrence, Calif.) to give 10 mg of compound 12 after lyophilization 65% yield.
Synthesis of Compound 14
Scheme 5
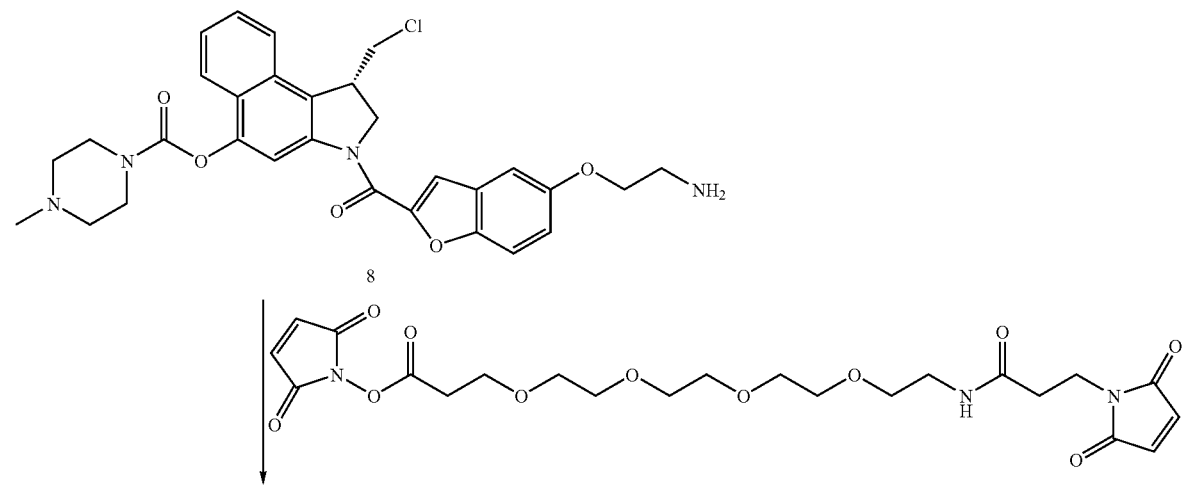

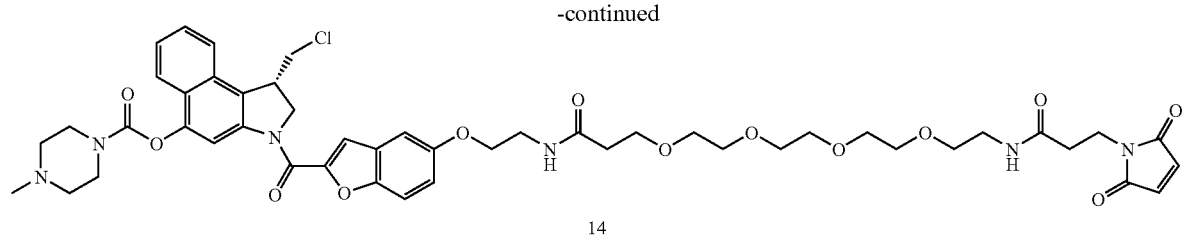
14
Compound 8 (4.8 mg, 0.0076 mMoles) was dissolved in DMF 1 mL followed by the addition of Mal-TEG-NHS ester (8 mg, 0.015 mMoles) as a solution in DCM (0.5 mL). 25-40 uL of DIPEA was added. The reaction was stirred for 30 minutes the solvent was evaporated and purified by reverse phase HPLC to give 4 mg of compound 14 (55% yield). Mass Spec: $M^{[+1]}$=962, $M^{[+Na]}$=984, $M^{[+K]}$
Synthesis of Compound 17
Scheme 6
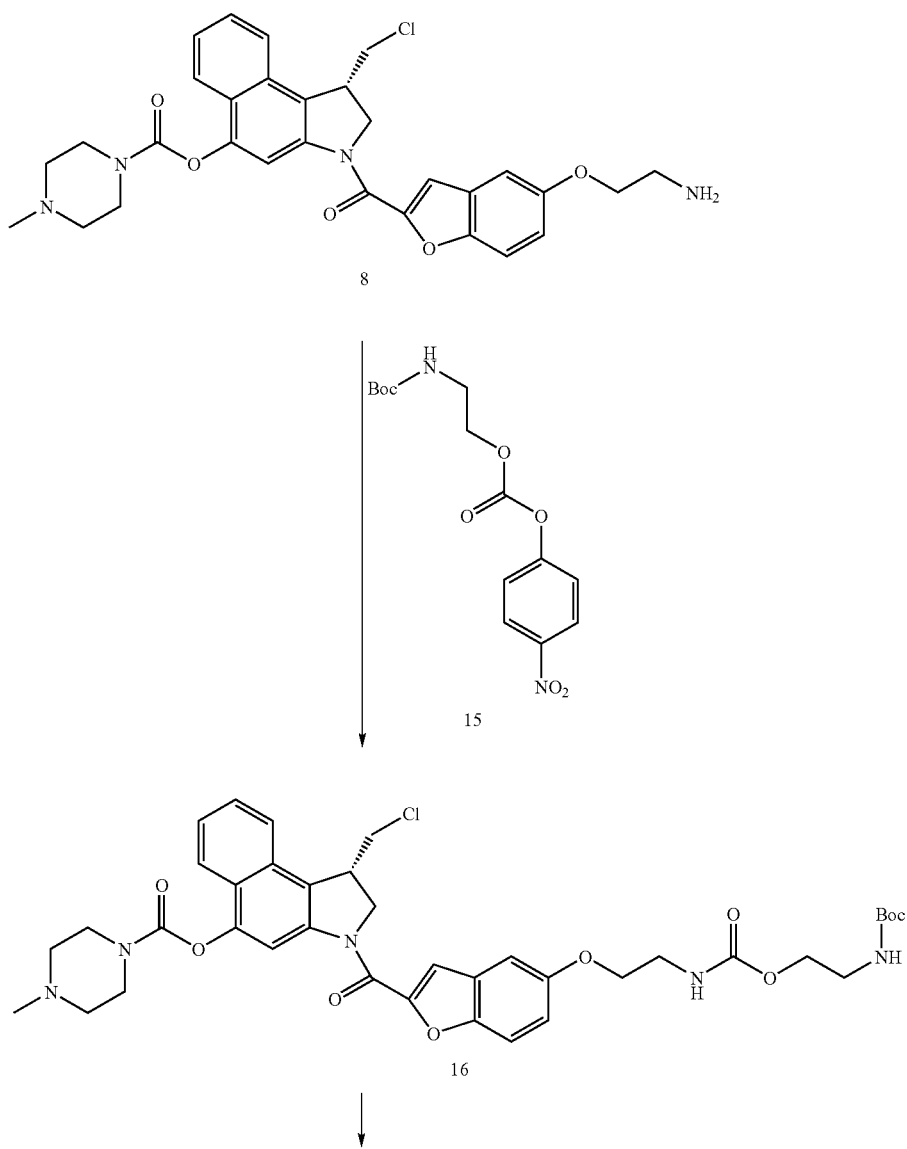

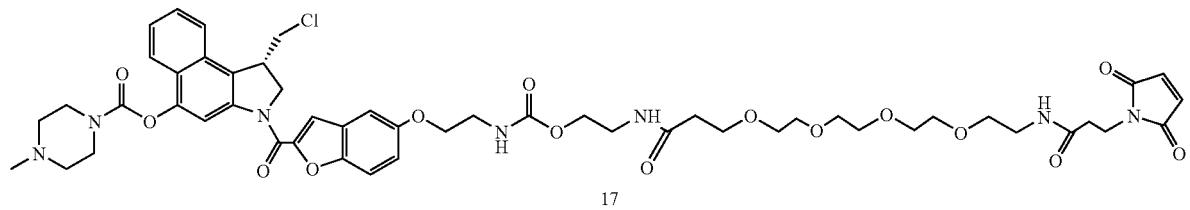

17

Tert-butyl 2-hydroxyethylcarbamate (270 mg, 1.675 mMoles) was dissolved in THF 10 mL. 4-Nitrophenyl chloroformate (674 mg, 3.35 mMoles) was added followed by dropwise addition of pyridine (400 μL, 5 mMoles). The reaction mixture was allowed to stir for 2 hours. The solvent was evaporated and crude purified by Silica Gel Flash Chromatography using DCM as eluent, giving 500 mg of compound 15 (92% yield). $H^1$ NMR, $CDCl_3$, 1.45 (s, 9H), 3.45 (m, 2H), 4.34 (m, 2H), 7.38 (d, 2H), 8.27 (d, 2H)

Compound 8 (0.018 mMoles) was dissolved in DMF 2 mL and compound 15 (11.6 mg, 0.035 mMoles) was added followed by the addition of 10-20 uL DIPEA. The reaction mixture was stirred for 6 hours the solvent was evaporated the purified with reverse phase HPLC to give 7 mg (52% yield) of compound 16. Mass Spec: $M^{[+1]}$ 750, $M^{[+Na]}=772$, $M^{[+K]}=788$. Compound 16 was deprotected using HCl-ethyl acetate and the solvent was evaporated and the product was dried overnight and used in the next reaction without any further purification. Mass Spec: $M^{[+1]}$ 651, $M^{[+Na]}=673$, $M^{[+K]}=688$. Crude product (0.009 mMoles) was dissolved in DMF 1 mL followed by addition of Mal-TEG-NHS ester (18 mg, 0.035 mMoles) as a solution in 0.5 mL DCM followed by DIPEA (10-20 uL). The reaction mixture was stirred for 15 minutes and the solvent was evaporated and purified by reverse phase HPLC to give 4.5 mg of compound 17 (48% yield). Mass Spec: $M^{[+1]}=1049$, $M^{[+Na]}=1071$, $M^{[+K]}=1087$ Each of the patent applications, patents, publications, and other published documents mentioned or referred to in this specification is herein incorporated by reference in its entirety, to the same extent as if each individual patent application, patent, publication, and other published document was specifically and individually indicated to be incorporated by reference.

While the present invention has been described with reference to the specific embodiments thereof, it should be understood by those skilled in the art that various changes may be made and equivalents may be substituted without departing from the true spirit and scope of the invention and the appended claims. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A compound of the formula

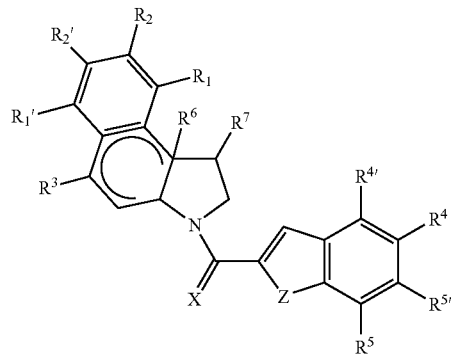

wherein X and Z are independently selected from O, S and $NR^{23}$ wherein $R^{23}$ is a member selected from H, substituted or unsubstituted alkyl, substituted or unsubstituted heteroalkyl, and acyl;

$R^1$ is H, substituted or unsubstituted lower alkyl, $C(O)R^8$, or $CO_2R^8$, $R^{1'}$ is H, substituted or unsubstituted lower alkyl, or C(O) $R^8$, each $R^8$ is a member independently selected from $NR^9R^{10}$ and $OR^9$ and $R^9$ and $R^{10}$ are members independently selected from H, substituted or unsubstituted alkyl and substituted or unsubstituted heteroalkyl;

$R^2$ is H, substituted or unsubstituted lower alkyl, unsubstituted heteroalkyl, cyano, or alkoxy;

$R^{2'}$ is H, substituted or unsubstituted lower alkyl, or unsubstituted heteroalkyl, $R^3$ is a member selected from the group consisting of $SR^{11}$, $NHR^{11}$ and $OR^{11}$, wherein $R^{11}$ is a member selected from the group consisting of H, substituted alkyl, unsubstituted alkyl, substituted heteroalkyl, unsubstituted heteroalkyl, diphosphates, triphosphates, acyl, C(O) $R^{12}R^{13}$, $C(O)OR^{12}$, $C(O)NR^{12}R^{13}$, $P(O)(OR^{12})_2$, C(O) $CHR^{12}R^{13}$, $SR^{12}$ and $SiR^{12}R^{13}R^{14}$, in which $R^{12}$, $R^{13}$, and $R^{14}$ are members independently selected from H, substituted or unsubstituted alkyl, substituted or unsubstituted heteroalkyl and substituted or unsubstituted aryl, or $R^{12}$ and $R^{13}$ together with the nitrogen or carbon atom to which they are attached are joined to form a substituted or unsubstituted heterocycloalkyl ring system having from 4 to 6 members;

$R^6$ is a single bond which is either present or absent and when present $R^6$ and $R^7$ are joined to form a cyclopropyl ring; and $R^7$ is CH$_2$—X or —CH$_2$— joined in said cyclopropyl ring with $R^6$, wherein $X^1$ is a leaving group, $R^4$, $R^{4'}$, $R^5$ and $R^{5'}$ are members independently selected from the group consisting of H, substituted alkyl, unsubstituted alkyl, substituted aryl, unsubstituted aryl, substituted heteroaryl, unsubstituted heteroaryl, substituted heterocycloalkyl, unsubstituted heterocycloalkyl, halogen, NO$_2$, NR$^{15}$R$^{16}$, NC(O)R$^{15}$, OC(O)NR$^{15}$R$^{16}$, OC(O)OR$^{15}$, C(O)R$^{15}$, SR$^{15}$, OR$^{15}$, CR$^{15}$=NR$^{16}$, and O(CH$_2$)$_n$NR$^{24}$R$^{25}$ wherein n is an integer from 1 to 20;

$R^{15}$ and $R^{16}$ are independently selected from H, substituted or unsubstituted alkyl, substituted or unsubstituted heteroalkyl, substituted or unsubstituted aryl, substituted or unsubstituted heteroaryl, substituted or unsubstituted heterocycloalkyl, and substituted or unsubstituted peptidyl, wherein $R^{15}$ and $R^{16}$ together with the nitrogen atom to which they are attached are optionally joined to form a substituted or unsubstituted heterocycloalkyl ring system having from 4 to 6 members, optionally containing two or more heteroatoms; and $R^{24}$ and $R^{25}$ are independently selected from hydrogen and unsubstituted alkyl, wherein at least one of $R^{24}$ and $R^{25}$ is hydrogen, and wherein at least one of $R^4$, $R^{4'}$, $R^5$ and $R^{5'}$ is O(CH$_2$)$_n$NR$^{24}$R$^{25}$.

2. The compound of claim 1, wherein $R^4$ is O(CH$_2$)$_n$NR$^{24}$R$^{25}$.

3. The compound of claim 2, wherein $R^4$ is O(CH$_2$)$_n$NH$_2$.

4. The compound of claim 3, wherein $R^{4'}$, $R^5$ and $R^{5'}$ are H.

5. The compound of claim 1, wherein $R^6$ is absent and $R^7$ is CH$_2$—X$^1$, wherein X$^1$ is F, Cl, or Br.

6. The compound of claim 1, wherein $R^1$, $R^{1'}$, $R^2$, and $R^{2'}$ are H.

7. The compound of claim 1, wherein X is O and Z is O.

8. The compound of claim 1, wherein the compound has the following formula:

9. The compound of claim 1, wherein the compound has the following formula:

wherein $X^1$ is F, Cl, or Br.

10. The compound of claim 1, wherein the compound has the following formula:

11. The compound of claim 1, wherein the compound has the following formula:

12. The compound of claim 1, wherein $R^2$ is CN.

13. The compound of claim 1, wherein $R^2$ is methyl.

14. The compound of claim 1, wherein X is O.

15. The compound of claim 1, wherein Z is O.

16. The compound of claim 1, wherein $R^{24}$ and $R^{25}$ are hydrogen.

17. A pharmaceutical formulation comprising a compound according to claim 1 and a pharmaceutically acceptable carrier.

18. The compound of claim 1, having the formula:

* * * * *